(12) United States Patent
Beachy et al.

(10) Patent No.: US 6,608,241 B1
(45) Date of Patent: Aug. 19, 2003

(54) PROTECTION OF PLANTS AGAINST VIRAL INFECTION

(75) Inventors: Roger N. Beachy, Ladue, MO (US); Robert T. Fraley, St. Louis, MO (US); Stephen G. Rogers, Chesterfield, MO (US)

(73) Assignees: Monsanto Technology LLC, St. Louis, MO (US); Washington University, St. Louis, MO (US)

( * ) Notice: Subject to any disclaimer, the term of this patent is extended or adjusted under 35 U.S.C. 154(b) by 0 days.

(21) Appl. No.: 06/917,027

(22) Filed: Oct. 9, 1986

Related U.S. Application Data

(63) Continuation-in-part of application No. 06/844,918, filed on Mar. 27, 1986, now abandoned, which is a continuation-in-part of application No. 06/792,389, filed on Oct. 29, 1985, now abandoned.

(51) Int. Cl.[7] .................. C12N 15/33; C12N 15/82; C12N 5/10; C12N 15/84; A01H 5/00
(52) U.S. Cl. .................. 800/280; 800/278; 800/294; 800/301; 435/411; 435/414; 435/415; 435/412; 435/417; 435/418; 435/419; 435/468; 435/469; 435/320.1; 435/252.2; 435/252.3; 536/23.72
(58) Field of Search .................. 435/68, 172.3, 435/317, 948, 240.4, 320, 69.1, 70.1, 252.2, 252.3, 320.1, 418, 419, 411, 414, 415; 800/1, 205, 250; 536/27, 23.72, 24.1; 935/29, 56, 67, 72

(56) References Cited

U.S. PATENT DOCUMENTS

| | | | |
|---|---|---|---|
| 4,407,956 A | * | 10/1983 | Howell .................. 435/172.3 |
| 5,580,716 A | | 12/1996 | Johnston et al. .................. 435/5 |
| 5,840,481 A | | 11/1998 | Johnston et al. .................. 435/5 |

FOREIGN PATENT DOCUMENTS

| | | | |
|---|---|---|---|
| AU | 57356786 | 11/1986 | .................. 435/172.3 |
| AU | 63924/86 | 4/1987 | .................. 435/172.3 |
| EP | 0 223 399 | 5/1986 | |
| EP | 0 240 331 | 10/1987 | |
| EP | 0 240 332 | 10/1987 | |
| EP | 242016 | 10/1987 | .................. 435/172.3 |
| WO | AU85/00093 | 1/1985 | |
| WO | 85 04 898 | 7/1985 | .................. 435/172.3 |
| WO | 86 05 516 | 9/1986 | .................. 435/172.3 |

OTHER PUBLICATIONS

Murphy et al. Viral Taxonomy, Springer–Verlag: New York, pp. 450–457, 1995.*
Wilson, T. BioEssays 10(6): 179–184, Jun. 1989.*
Beachy, et al.; Potential for Applying Genetic Transformation to Studies of Viral Pathogenesis and Cross–Protection; Biotechnology in Plant Science (1985); pp. 265–275.

(List continued on next page.)

*Primary Examiner*—David T. Fox
(74) *Attorney, Agent, or Firm*—Grace L. Bonner; Howrey Simon Arnold & White, LLP

(57) ABSTRACT

The invention involves recombinant, double-stranded DNA that contains a promoter which functions in plant cells to cause the production of RNA sequences of a plant virus, a DNA sequence that causes the production of an RNA sequence encoding the coat protein of said plant virus, and a 3' non-translated region which functions in plant cells to cause the addition of polyadenylated nucleotides to the 3' end of said RNA sequence; which double-stranded DNA can be used in a method for genetically transforming plants to produce genetically transformed plant cells and plants that are resistant to virus infection.

40 Claims, 17 Drawing Sheets

OTHER PUBLICATIONS

Beachy, R. N., et al; "Potential for applying genetic transformation to studies of viral pathogenesis and cross–protection" (1987); Chemical Abstracts, vol. 106, No. 1, p. 134, ref. No. 1337j; and Biotechnol Plant Sci: Relevance Agric. Eighties, 1985.

Hamilton, R.I.; "Using plant viruses for disease control"; (1985) Hortscience, vol. 20, No. 5, pp. 848–852.

Bialy, H., et al.; "A new route to virus resistance in plants"; (1986); Biotechnology, vol. 4, p. 96.

Abel, P.P. et al.; "Dielay of disease development in transgenic plants that express the tobacco mosaic virus coat protein gene"; 1986; Science, vol. 232, pp. 738–743.

Loesch–Fries, L.S. et al; "Cloning of alfalfa mosaic virus coat protein gene and anti–sense RNA into a binary vector and their expression in transformed tobacco tissue"; Journal of Cell. Biochem., vol. 0, No. 10, part C, p. 41, ref. No. J108.

Bevan, M.W. et al.; "Expression of tobacco mosaic virus coat protein by a cauliflower mosaic virus promoter in plants transformed by Agrobacterium"; The EMBO Journal (1985); vol. 4, No. 8, pp 1921–1926.

Zaitlin, Milton, 1976, Viral Cross Protection: More Understanding is Needed, Phytopathology 66:382–383.

S. Sarkar and P. Smitamana, 1981, A Proteinless Mutant of Tobacco Mosaic Virus: Evidence Against the Role of a Viral Coat Protein for Interference, Mol Gen Genet 184:158 & 159.

J. C. Sanford and S. A. Johnston, 1985, The Concept of Parasite–Derived Resisitance—Deriving Resistance Genes from the Parasite's Own Genome, J. theo. Biol. 113: 395–405.

M.W. Bevan, S.E. Mason and P. Goelet, 1985, Expression of tobacco mosaic virus coat protein by a cauliflower mosaic virus promoter in plants transformed by Agrobacterium, The EMBO Journal, vol. 4, No. 8, pp. 1921–1926.

DeBlock et al. 1984. The EMBO J 3(8): 1681–1689.*

Herrera–Estrella et al. 1983. EMBO J 2(6):987–995.*

Herrera–Estrella et al. 1984. Nature 310: 115–120.*

Velten et al. 1984. EMBO J 3(12): 2723–2730.*

Sherwood et al. 1982. Virology 119:150–158.*

Koziel et al. 1984. J. Mol. Appl. Genet. 2(6): 549–562.*

Meshi et al. 1982. Virology 118: 64–75.*

Hamilton et al. 1984. EMBO J 3: 2197–2205.*

Herbomel et al. 1983. Chem. Abst. 100 (5): #30430r.*

Goodman et al. 1987. Science 236: 48–54.*

Agnòs, G. 1978. p. 585 Dr: Plant Pathology, vol. 2 Academic Press, Inc.: New York.*

Palukaitis et al. 1984. pp. 420–429 In: Plant–microbe interact. vol. 1, Kosuge et al., eds, Macmillan: New York.*

Izant et al. 1984. Cell 36: 1007–1015.*

Chang et al. 1985. Mol. Cell. Biol. 5(9): 2341–2348.*

* cited by examiner

N-terminus ———— estimate 60-100 bp ————————————

```
 P   K   K   S   T   S   S   S   K   S   A   S   T   S   S
CCA AAG AAG AGC ACC AGT AGT AGT AAG GGA GCT GGC ACA AGC AGC

K   D   V   N   V   S   S   K   S   K   V   V   P   R   L
AAA GAT GTA AAT GTT GGA TCA AAG GGA AAG GTG GTT CCG CGT TTG

Q   K   I   T   R   K   M   N   L   P   M   V   E   G   N
CAG AAG ATT ACA AGA AAG ATG AAT CTT CCA ATG GTT GAA GGG AAC

I   I   L   S   L   D   H   L   L   E   Y   K   P   N   Q
ATC ATC CTC AGT TTG GAC CAC TTG CTT GAG TAC AAA CCT AAT CAG
```

———————————————— 90 bp ————————————————

```
             A   D   G   V   V   M   N   G   F   M   V   W   C
—— ——       GCA GAT GGT GTG GTT ATG AAT GGC TTC ATG GTA TGG TGC

I   D   N   G   T   S   P   D   A   N   G   V   W   V   M
ATT GAC AAT GGT ACA TCT CCA GAT GCT AAT GGC GTG TGG GTG ATG

M   D   G   E   E   Q   I   E   Y   P   L   K   P   -   -
ATG GAT GGA GAG GAA CAG ATT GAA TAT CCG CTG AAA CCC ——  ——

S   K   C   K   T   N   L   R   Q   I   M   H   H   F   S
TCG AAA TGC AAA ACC AAC TTG AGA CAA ATC ATG CAC CAT TTC TCA

D   A   A   E   A   Y   I   E   M   R   N   S   E   S   P
GAT GCA GCA GAA GCT TAC ATT GAG ATG AGA AAT TCT GAA AGT CCG

Y   M   P   R   Y   G   L   L   R   N   L   R   D   R   E
TAT ATG CCT AGA TAT GGA CTA CTG AGG AAT TTG AGA GAT AGA GAG

L   A   R   Y   A   F   D   F   Y   E   V   T   S   K   T
CTA GCT CGC TAT GCT TTT GAT TTC TAT GAG GTT ACT TCT AAA ACA

P
CCA AA-
```

———————————————— 100 bp ————————————————

```
     E   R   H   T   A   R   D   V   N   Q   N   M   H   T
-AT GAA AGG CAC ACT GCA AGG GAT GTG AAT CAA AAC ATG CAC ACT

L   L   G   M
CTT TTG GGC ATG
```

GGC— ——  ——■ TAAAG GCTAA GTAAA TTGGT CACAG TTATC ATTTC

GGGTC GCTTT ATAGT TTACT ATAAT ATAGT AGTTG CACTG TCTTT AAATA

TAGTG TGATT GCATC ACCAA ATAAA TGTTT TTGTT TAGTG TGGTT TTAAC

CACCC CAGTG TGCTT TATGT TATAG TTTAT GAATG GCAGG GAGAA CCATT

GTGTT GCCGG AGCCC TTTGA AGAGT GATTT CATCA CGTCT AGTGG CCGAG

GTGCG GCAAT GTTTG TTGTC CTAAA poly A

Figure 2

CaMV 36S PROMOTER

Filled EcoRI 1                                                                                                           70
GAATTAATTCCCGATCcTATCTGTCACTTCATCAAAAGGACAGTAGAAAAGGAAGGTGGCACTACAAATG 71                                                                                                          140
CCATCATTGCGATAAAGGAAAGGCTATCGTTCAAGATGCCTCTGCCGACAGTGGTCCCAAAGATGGACCC 141                                                                                                         210
CCACCCACGAGGAGCATCGTGGAAAAAGAAGACGTTCCAACCACGTCTTCAAAGCAAGTGGATTGATGTG
                                                                                                    TATA
211                                                                                                    | 280
ATATCTCCACTGACGTAAGGGATGACGCACAATCCCACTATCCTTCGCAAGACCCTTCCTCTATATAAGG
                    CAP Site
281                    |                         332
AAGTTCATTTCATTTGGAGAGGACACGCTGAAATCACCAGTCTCTCTCTACA

SYNTHETIC MULTI-LINKER

BgIII   ClaI  SmaI KpnI XhoI  EcoRI
   |       |     |    |    |      |
AGATCTATCGATTCCCGGGTACCTCGAGAATTCCC

NOS 3' POLYADENYLATION SIGNAL 368                                                                                                  430
       GATCGTTCAAACATTTGGCAATAAAGTTTCTTAAGATTGAATCCTGTTGCCGGTCTTGCGATG 431                                                                                                         500
ATTATCATATAATTTCTGTTGAATTACGTTAAGCATGTAATAATTAACATGTAATGCATGACGTTATTA
                    3' End mRNA
501                 |  |    ||||||||                                                                        570
TGAGATGGGTTTTTTATGATTAGAGTCCCGCAATTATACATTTAATACGCGATAGAAAACAAAATATAGCG 571                                                                                                         640
CGCAAACTAGGATAAATTATCGCGCGCGGTGTCATCTATGTTACTAGATCggggatccgtcgacctgcag
    HindIII
641 | 648

Figure 4

Synthesis of AMV coat protein cDNA
Hybridization of Synthetic Primer to RNA 4, reverse transcription
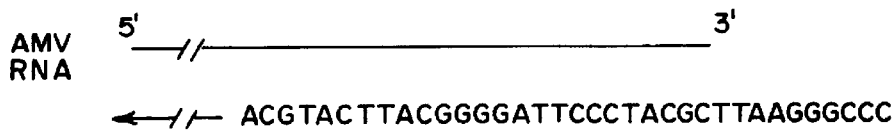
Base Hydrolysis of RNA, hybridization of second strand primer, synthesis of second strand
EcoRI digestion
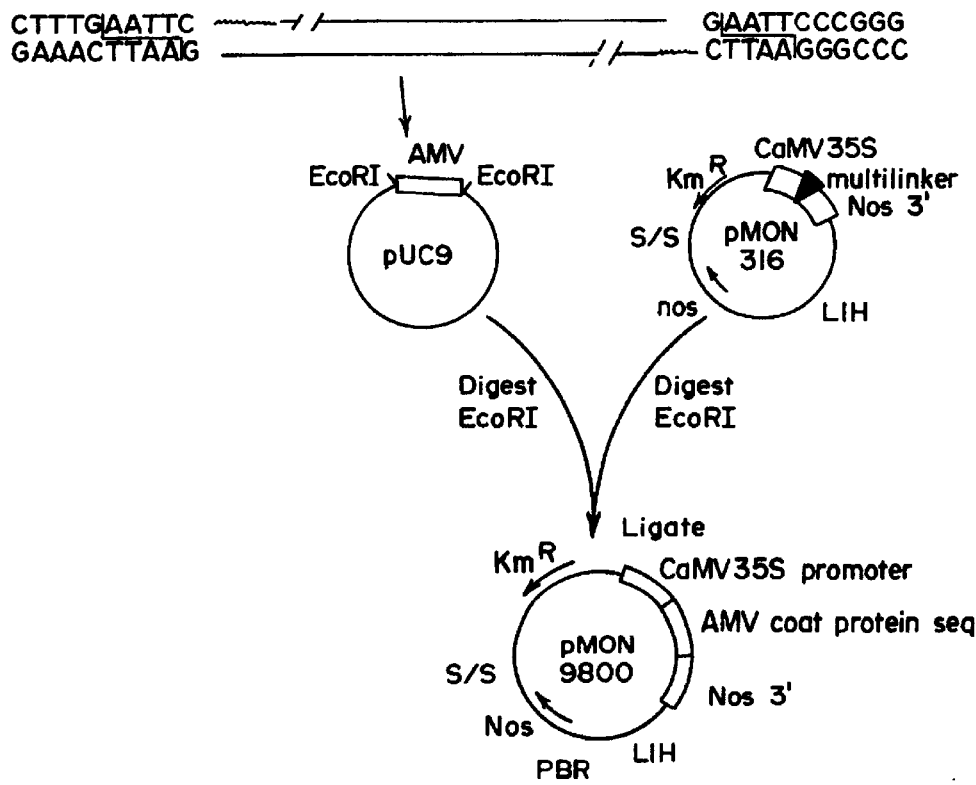
Figure 13

Figure 15

PROTECTION OF PLANTS AGAINST VIRAL INFECTION

This is a continuation-in-part of application Ser. No. 844,918 (filed Mar. 27, 1986) now abandoned, which is a continuation-in-part of application Ser. No. 792,389 (filed Oct. 29, 1985) now abandoned.

BACKGROUND OF THE INVENTION

The present invention relates to a method for producing plants that are resistant to virus disease, to genetic material used in imparting such virus resistance, and to products of the method. Accordingly, the present invention involves applications from the fields of plant molecular biology, plant virology, and plant genetic engineering.

Virus infections in plants cause a variety of detrimental effects, including stunted growth, altered morphology, and reduced yields. In addition, virus infections often leave plants more susceptible to damage by other pests and pathogens. For general information on plant viruses, see, e.g., Matthews (1981), Lauffer (1981) and Kado & Agrawal (1972).

Plants do not have immune systems involving antibodies, like animals. However, plants have evolved several methods of resisting infection by pathogens. For example, some types of plants create lectins, which bind to saccharide moieties on the surfaces of invading fungi, and immobilize the fungi. In addition, some types of plants apparently create various molecules which circulate through the plant in response to attacks by bacteria, insects, and possibly viruses.

It is possible to induce some degree of virus resistance in some types of plants by infecting young plants with an "attenuated" strain of a virus, i.e., a strain of the virus which does not cause severe symptoms; see, e.g., Rast (1972) and Costa (1980).

This approach has several limitations, including: (1) it can conveniently be used only in certain types of crops; (2) it can be used only with certain types of viruses; (3) it can be used only if a suitably attenuated strain of the infecting virus has been identified and isolated; (4) the protection provided by this method may be effective only against a limited number of different viruses; and (5) attenuated infection can severely aggravate an infection caused by a second, unrelated virus in a synergistic interaction.

There is, therefore, a need for a method of protecting plants from virus infection that overcomes the above-summarized problems and that does not require identification, isolation, or use of an attenuated virus. There is also a need for conferring virus resistance where natural genetic or cross-protection resistance is unavailable.

SUMMARY OF THE INVENTION

Accordingly, it is an object of the present invention to provide a method for producing virus resistant plants that does not depend on the use of an attenuated virus, the existence of a genetic determinant conferring resistance, or the availability of cross-protection.

It is also an object of the present invention to provide a method for genetically engineering plants by insertion into the plant genome of a DNA construct containing, inter alia, a small portion of a plant viral genome, such that the engineered plants display resistance to the plant virus.

It is another object of the present invention to provide a recombinant DNA molecule which can be used to produce genetically transformed, virus-resistant plants.

It is still another object of the present invention to provide genetically transformed cells and differentiated plants that are characterized, respectively, by the presence of a DNA sequence that causes the production of an RNA sequence of a plant virus.

In accomplishing the foregoing objects, there has been provided, in accordance with one aspect of the present invention, a method of producing genetically transformed plants which are resistant to infection by a plant virus, comprising the steps of
 (a) inserting into the genome of a plant cell a recombinant, double-stranded DNA molecule comprising
  (i) a promoter which functions in plant cells to cause the production of RNA sequences of the plant virus,
  (ii) a DNA sequence derived from the plant virus that causes the production of an RNA sequence of the plant virus, and
  (iii) a 3' non-translated DNA sequence which functions in plant cells to cause the addition of polyadenylated nucleotides to the 3' end the RNA sequence;
 (b) obtaining transformed plant cells; and
 (c) regenerating from the transformed plant cells genetically transformed plants which have increased resistance to infection by the plant virus.

In one preferred embodiment, the RNA sequence of the plant virus encodes a coat protein of that virus.

In accordance with another aspect of the present invention, there has been provided a recombinant, double-stranded DNA molecule comprising in sequence:
 (a) a promoter which functions in plant cells to cause the production of RNA sequences of a plant virus;
 (b) a DNA sequence derived from the plant virus that causes the production of an RNA sequence, the RNA sequence encoding the coat protein of the plant virus; and
 (c) a 3' non-translated region which functions in plant cells to cause the addition of polyadenylated nucleotides to the 3' end of the RNA sequence.

There has also been provided, in accordance with another aspect of the present invention, bacterial and transformed plant cells that contain, respectively, DNA comprised of the above-mentioned elements (a), (b) and (c).

In accordance with yet another aspect of the present invention, a differentiated plant has been provided that comprises transformed plant cells, as described above, which exhibit resistance to the plant virus. According to still another aspect of the present invention, a process is provided that entails cultivating such a plant and, in addition, and propagating such plant using propagules such as explants, cuttins and seeds or crossing the plant with another to produce progeny that also display resistance to the plant virus.

Other objects, features and advantages of the present invention will become apparent from the following detailed description. It should be understood, however, that the detailed description and the specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

FIG. 2 shows a partial amino acid sequence of the soybean mosaic virus coat protein (SMV CP).

FIG. 4 depicts the complete sequence of CaMV35S promoter, multilinker and nopaline synthase segment illustrated in FIG. 3.

FIG. 13 represents a process used to prepare cDNA coding for the coat protein of alfalfa mosaic virus (AMV CP).

FIG. 15 shows the nucleotide sequence of the PVX CP gene.

DETAILED DESCRIPTION OF THE PREFERRED EMBODIMENTS

Figure 1:
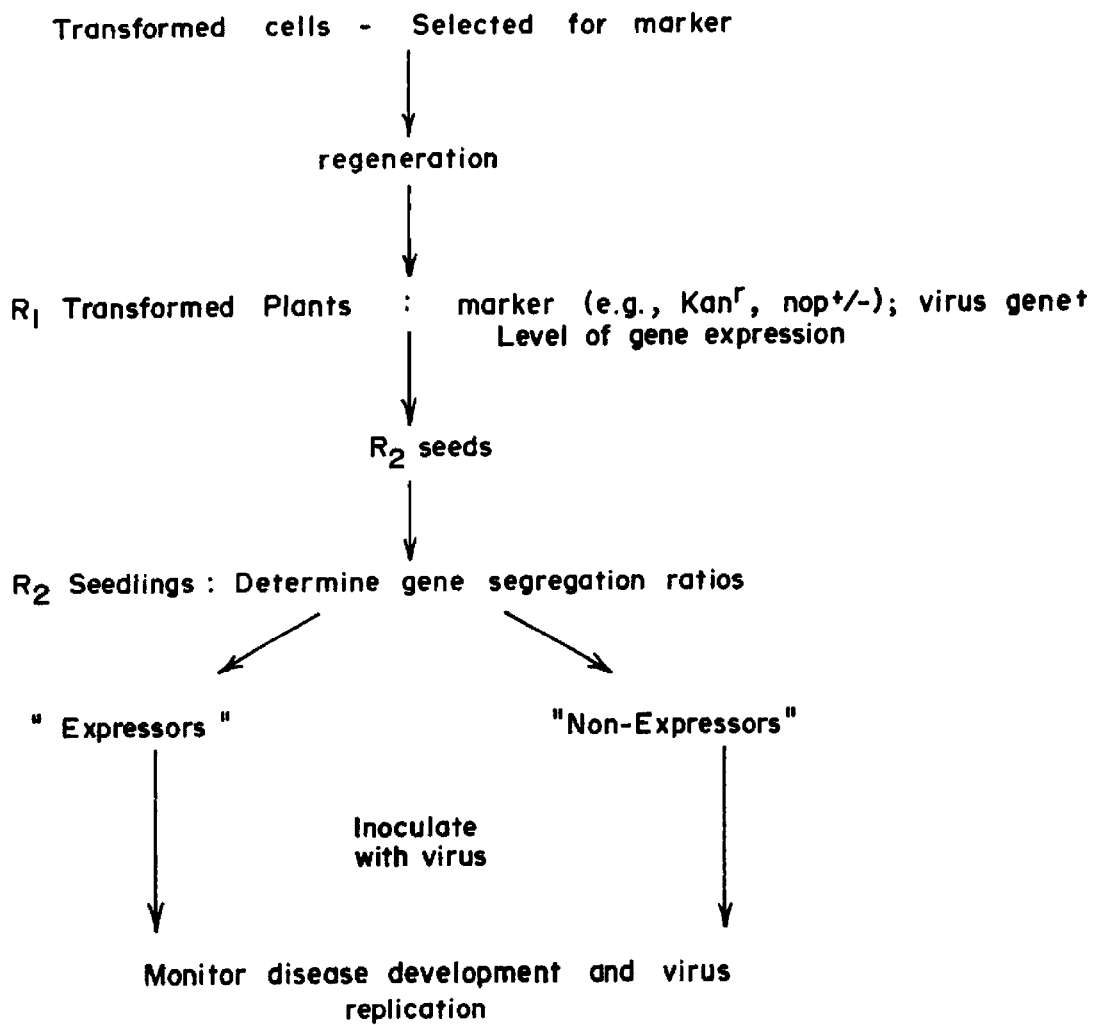
FIG. 1 provides a graphic outline for a biological assay for virus disease resistance in transgenic plants.

The present invention involves the preparation of DNA constructs that function in plant cells and produce virus resistance. As explained in greater detail below, the phrase "virus resistance" is used here to refer to the ability of a plant to resist one or more types of plant viruses.

Numerous plant viruses cause significant crop losses worldwide. This invention provides a method for protecting plants susceptible to infection by plant viruses. Exemplary of such plant viruses are soybean mosaic virus, bean pod mottle virus, tobacco ring spot virus, barley yellow dwarf virus, wheat spindle streak virus, soil born mosaic virus, wheat streak virus in maize, maize dwarf mosaic virus, maize chlorotic dwarf virus, cucumber mosaic virus, tobacco mosaic virus, alfalfa mosaic virus, potato virus X, potato virus Y, potato leaf roll virus and tomato golden mosaic virus. Among these, protection against maize dwarf mosaic virus, barley yellow dwarf virus, wheat streak mosaic virus, soil born mosaic virus, potato leafroll virus and cucumber mosaic virus is particularly important.

Plants which can be made virus resistant by practice of the present invention include, but are not limited to, potato, tomato, pepper, tobacco, soybean, wheat, corn, citrus, squash, cucumber and beet.

The expression of a plant gene which exists in double-stranded DNA form does involve transcription of messenger RNA (mRNA) from one strand of the DNA by RNA polymerase enzyme, and the subsequent processing of the mRNA primary transcript inside the nucleus. This processing involves a 3' non-translated region which adds polyadenylate nucleotides to the 3' end of the viral RNA.

Transcription of DNA into mRNA is regulated by a region of DNA usually referred to as the "promoter." The promoter region contains a sequence of bases that signals RNA polymerase to associate with the DNA, and to initiate the transcription of mRNA using one of the DNA strands as a template to make a corresponding strand of RNA.

A number of promoters which are active in plant cells have been described in the literature. These include the nopaline synthase (NOS) and octopine synthase (OCS) promoters (which are carried on tumor-inducing plasmids of *Agrobacterium tumefaciens*), the cauliflower mosaic virus (CaMV) 19S and 35S promoters, the light-inducible promoter from the small subunit of ribulose bis-phosphate carboxylase (ssRUBISCO, a very abundant plant polypeptide), and promoters of genes encoding hydroxyproline-rich glycoproteins. All of these promoters have been used to create various types of DNA constructs which have been expressed in plants; see, e.g., PCT publication WO 84/02913 (Rogers et al, Monsanto).

Promoters which are known or are found to cause transcription of viral RNA in plant cells can be used in the present invention. Such promoters may be obtained from plants or viruses and include, but are not limited to, the CaMV35S promoter and promoters isolated from plant genes such as ssRUBISCO genes. As described below, it is preferred that the particular promoter selected should be capable of causing sufficient expression to result in the production of an effective amount of coat protein to render the plant substantially resistant to virus infection. The amount of coat protein needed to induce resistance may vary with the type of plant and/or the virus to be protected against. Accordingly, while the CaMV35S promoter is preferred, it should be understood that this promoter may not be the optimal one for all embodiments of the present invention.

The promoters used in the DNA constructs of the present invention may be modified, if desired, to affect their control characteristics. For example, the CaMV35S promoter may be ligated to the portion of the ssRUBISCO gene that represses the expression of ssRUBISCO in the absence of light, to create a promoter which is active in leaves but not in roots. The resulting chimeric promoter may be used as described herein. For purposes of this description, the phrase "CaMV35S" promoter thus includes variations of CaMV35S promoter, e.g., promoters derived by means of ligation with operator regions, random or controlled mutagenesis, etc.

The DNA constructs of the present invention preferably contain, in double-stranded DNA form, a portion of the virus genome that encodes the coat protein of a virus. Although most types of plant viruses contain RNA rather than DNA, others contain single- or double-stranded DNA. Viruses which contain RNA do not contain genes with standard transcriptional promoters and/or 3' regulatory sequences. In these cases, the polypeptides or proteins are translated directly from the RNA strand carried by the virus or its complement. The portion of the virus genome which encodes the coat protein can be determined by one of several known methods well within the skill of the art (see Example 1 below).

For instance, in some cases one may choose to sequence the coat protein and synthesize a DNA sequence that encodes the coat protein of the virus. Alternatively, one may identify and purify RNA from the virus that encodes the coat protein. In the vast majority of RNA-containing plant viruses, the coat protein gene is located at the 3' end of the viral RNA. In some cases, the coat protein gene could be located by using an oligonucleotide probe, the sequence of which reflects the amino-acid sequence of the viral coat protein. If the virus carries RNA, the DNA coding sequence can be obtained using the enzyme reverse transcriptase to form complementary DNA (CDNA). As indicated above, most types of plant viruses contain RNA, including tobacco mosaic virus, tomato spotted wilt virus, cucumber mosaic virus, alfalfa mosaic virus, potexviruses like potato virus X, potyviruses like potato virus Y, and potato leafroll virus.

In the case of some viruses, such as potyviruses, the coat protein is part of a polyprotein which is processed to release the coat protein. Those skilled in the art should take this into account to isolate the region of the virus genome that encodes the coat protein and to introduce translation initiation signals, as detailed in Example 1 below.

Although less preferred, the sequence used in a DNA construct within the present invention which causes the production of a virus RNA sequence may be in the anti-sense configuration. For example, the RNA produced by transcription of the DNA could ultimately produce an RNA molecule which has the complementary sequence of the native viral coat protein mRNA. (It is believed that, if the anti-sense configuration is used, the DNA sequence may be shortened to produce an anti-sense RNA complementary to the 5' region of the coat protein mRNA.) Alternatively, the anti-sense DNA can be derived from other segments of the virus genome; preferred regions would include the 5' end of the viral RNA, which regions have been shown in vitro to inhibit translation of viral RNA (Beachy et al (1985)). In either case, this configuration is less preferred because the anti-sense transcript is believed to be less stable or to require higher levels of expression in the host plant.

A coding sequence used in a DNA construct of this invention may be modified, if desired, to create mutants, either by random or controlled mutagenesis, using methods known to those skilled in the art. Such mutants and variants are therefore within the scope of the present invention. Accordingly, the phrase "coat protein" is used here to include truncated proteins and fusion proteins, as well as unmodified coat protein.

The 3' non-translated region contains a polyadenylation signal which functions in plants to cause the addition of polyadenylate nucleotides to the 3' end of the viral RNA. Examples of suitable 3' regions are (1) the 3' transcribed, non-translated regions containing the polyadenylated signal of Agrobacterium the tumor-inducing (Ti) plasmid genes, such as the nopaline synthase (NOS) gene, and (2) plant genes like the soybean storage protein genes and the small subunit of the RuBP carboxylase gene. An example of a preferred 3' region is that from the NOS gene, described in greater detail in the examples below.

The RNA produced by a DNA construct of the present invention also contains a 5' non-translated leader sequence. This sequence can be derived from the promoter selected to express the gene, and can be specifically modified so as to increase translation of the mRNA. The 5' non-translated regions can also be obtained from viral RNA's, from suitable eukaryotic genes, or from a synthetic gene sequence. The present invention is not limited to constructs, as presented in the following examples, wherein the non-translated region is derived from both the 5' non-translated sequence that accompanies the promoter sequence and part of the 5' non-translated region of the virus coat protein gene. Rather, the non-translated leader sequence can be part of the 5' end of the non-translated region of the coding sequence for the virus coat protein, or part of the promoter sequence, or can be derived from an unrelated promoter or coding sequence as discussed above.

A DNA construct of the present invention can be inserted into the genome of a plant by any suitable method. Suitable plant transformation vectors include those derived from a Ti plasmid of *Agrobacterium tumefaciens*, as well as those disclosed, e.g., by Herrera-Estrella (1983), Bevan (1983), Klee (1985) and EPO publication 120,516 (Schilperoort et al). In addition to plant transformation vectors derived from the Ti or root-inducing (Ri) plasmids of Agrobacterium, alternative methods can be used to insert the DNA constructs of this invention into plant cells. Such methods may involve, for example, the use of liposomes, electroporation, chemicals that increase free DNA uptake, and transformation using viruses or pollen.

In one embodiment of the present invention, a double-stranded cDNA sequence is prepared from an RNA segment (CP-mRNA) that encodes the coat protein of tobacco mosaic virus (TMV). This coding sequence can be ligated to a CaMV35S promoter, and to a NOS 3' non-translated region, to form a DNA construct within the present invention. The DNA construct is inserted into an intermediate plasmid derived in part from a Ti plasmid of *Agrobacterium tumefaciens*, to create plasmid pMON319. The vector is then inserted into cultured *A. tumefaciens* cells which contain a disarmed Ti plasmid. The two plasmids formed a cointegrate plasmid by means of a crossover event.

Bacterial cells containing the cointegrate plasmid were cultivated together with cells derived from tobacco plants, and transformed plant cells were selected by means of nutrient media containing kanamycin. The cells were then cultured into callus tissue, and regenerated into differentiated plants. The resulting plants of the present invention contain the DNA construct, which imparts virus resistance.

In practicing the present invention, the resistance-imparting capabilities of a DNA construct, which can contain a CP-encoding sequence from a particular virus, is preferably assessed, in the first instance, using a systemic host for that virus. In a "systemic" host plant, the virus has the ability to replicate and move, by an as-yet unspecified process, from the inoculation site (typically, on a leaf) throughout the plant, engendering symptoms of infection which are systemic rather than localized. (Conversely, a "nonsystemic" host displays symptoms, like the development of necrotic spots, that are restricted to the region around the inoculation site.) The pairing of specific viruses with hosts that are systemic to those viruses is well-recognized in plant pathology. It is known, for example, that most tomato and tobacco varieties, as well as alfalfa, are systemic hosts for alfalfa mosaic virus (AMV); that the cucumber mosaic virus (CuMV) systemically infects tomato, tobacco, cucumber and other melon crops; and that tobacco, tomato and numerous orchid varieties are systemic hosts for TMV. See, generally, INDEX OF PLANT VIRUS DISEASES, Agriculture Handbook No. 307 (ARS-USDA 1966).

More specifically, a DNA construct prepared in accordance with the present invention is preferably introduced, via a suitable vector as described above, into plant cells or protoplasts derived from a plant that is a systemic host for the virus used as the source for a DNA sequence in the construct that causes the production of an RNA sequence. If the DNA sequence encodes virus coat protein, then the plant material thus modified can be assayed, for example, by Northern blotting, for the presence of CP-mRNA; if no CP-mRNA (or too low a titer) is detected, the promoter used in the construct to control the CP-encoding segment can be replaced with another, potentially stronger promoter, and the altered construct retested.

Alternatively, this monitoring can be effected in whole regenerated plants. In any event, when adequate production of virus mRNA is achieved, and the transformed cells (or protoplasts) have been regenerated into whole plants, the latter are screened for resistance to the virus. Choice of methodology for the regeneration step is not critical, with suitable protocols being available for hosts from Leguminosae (alfalfa, soybean, clover, etc.), Umbelliferae (carrot, celery, parsnip), Cruciferae (cabbage, radish, rapeseed, etc.), Cucurbitaceae (melons and cucumber), Gramineae (wheat, rice, corn, etc.), Solanaceae (potato, tobacco, tomato, peppers) and various floral crops. See, e.g., Ammirato et al (1984). Plants from each of the aforesaid families can be rendered virus-resistant pursuant to the present invention.

Regenerated plants which are tested for virus resistance are preferably exposed to the virus at a concentration that is in a range where the rate of disease development correlates linearly with virus concentration in the inoculum. This linear range can be determined empirically, using nontransformed plants for a given pairing of virus and host species.

Methods for virus inoculation are well-known to those skilled in the art, and are reviewed by Kado & Agrawal (1972). One method involves abrading a leaf surface with an aqueous suspension (typically buffered at pH 7–8) containing an abrasive material, such as carborundum or diatomaceous earth, and the virus. While inoculation in this manner is generally preferred for its simplicity, those skilled in the art will recognize that other approaches may be preferable for certain plant viruses. For example, the aphid-born potato leafroll virus is known not to be readily inoculated by mechanical abrasion; rather, it is transferred using appropriate insect vectors. See, generally, Thomas (1983).

Progeny of regenerates are inoculated and observed with similarly treated controls, which can be untransformed plants and/or plants transformed with a construct lacking the DNA sequence that causes the production of a virus RNA sequence, to determine comparative resistance, e.g., as reflected in a difference between the groups as to the timing of onset of symptoms (see FIG. 1). For example, it has been found that plants containing the virus coat protein coding sequence, in accordance with the present invention, exhibit symptoms of viral infection, relative to control plants, only after a substantially longer time, if at all. Observed resistance among transgenic plants can be correlated with measured levels of virus mRNA or coat protein. Thus, it has been discovered that expression of a small portion of the viral genome can confer resistance to virus infection.

In some cases, expression of viral mRNA or coat protein may not be detectable. This may be due to an instability in the mRNA or protein. There are methods known to those skilled in the art, however, for stabilizing mRNA and proteins. For example, the splicing of introns is known to play an important role in the formation of stable mRNA (Hamer & Leder (1979)). The expression of the virus coat protein gene may be substantially enhanced by insertion of introns in either the coding or the noncoding sequences. Furthermore, sequences in the 3' untranslated sequences of the mRNA's are known to determine the stability of the corresponding mRNA's (Shaw & Kamen (1986)). The stability of the engineered coat protein mRNA may be substantially increased by alteration of its 3' untranslated region. Finally, it is known that several proteins retain their functional activity upon proteolysis (Moore (1981); Sandmeier (1980); Zurini (1984)). The truncated coat protein molecules produced according to the present invention could retain their biological activity and confer virus resistance when expressed at high levels in transgenic plants.

EXAMPLE 1

Typical Isolation of a Virus Coat Protein Gene for Use in Cross-Protection

The potyviruses comprise the most wide-spread and economically important group of known plant viruses. A potyvirus, the soybean mosaic virus (SMV), was therefore selected to illustrate a general approach for isolating a small portion of the virus genome, the sequence coding for coat protein, which can be used to impart virus disease resistance ("cross-protection") pursuant to the present invention (see FIG. 1).

SMV was purified from soybean leaves which had been infected with the N strain of SMV. Virus was isolated, and viral RNA prepared, following the procedures disclosed by Vance & Beachy (1984). Antibody to SMV was raised in rabbits by conventional methodology, which included the injection of 1 mg of purified SMV into rabbits, followed four weeks later by a second injection of 50/ug of SMV, and two weeks thereafter by an additional injection (50/ug) of SMV. Serum was collected for use in this example at two-week intervals after the final booster injection.

The cDNA cloning of virus coat protein genes was accomplished using methods familiar to those skilled in the art. cDNA was produced from viral RNA by first priming the polyadenylated SMV RNA with oligo-dT and then producing cDNA with reverse transcriptase. To produce double-stranded CDNA, the first strand cDNA:RNA hybrid molecule was treated with RNase H and DNA polymerase I. The molecules were then treated with T4 DNA polymerase, followed by EcoRI methylase. The molecules were then reacted with T4 DNA ligase in the presence of synthetic oligonucleotide linkers containing the EcoRI site. The molecules were thereafter digested with EcoRI and ligated to the plasmid pEMBL18, one of a class of widely-available cloning vectors constructed in the European Molecular Biology Laboratory, P.O. Box 10-2209, 6900 Heidelberg, Federal Republic of Germany. The pEMBL18 DNA had previously been restricted with the enzyme EcoRI and treated with alkaline phosphatase to prevent reannealing of the plasmid. Double-stranded cDNA's with EcoRI sites exposed were then ligated to the opened plasmid. These ligated cDNA's were then used to transform *E. coli* strain DH5α.

Colonies of the transformed bacteria were screened with $^{32}$P-labeled CDNA, and those that reacted with the $^{32}$P-labeled molecules were selected. To screen for antigen production, IPTG was used to induce positive transformants, and the growing colonies were screened, via an antibody blot procedure, with the rabbit anti-coat protein antibodies previously raised. (Certain suitable anti-CP antibodies can also be obtained commercially, e.g., from the American Type Culture Collection in Rockville, Md.) Those colonies that reacted with the antibody were selected for further screening to confirm that they actually produced a coat protein:lacZ fusion protein. Plasmid DNA isolated from colonies that produced a fusion protein was used as a probe to identify other colonies containing cDNA's which overlapped with those using standard hybridization techniques (Maniatis et al (1982)).

The DNA sequence of the cloned cDNA's was determined by standard procedures, see FIG. 2. Amino-acid sequencing of the viral coat protein can be completed to determine its NH$_2$-terminal amino acid sequence. Since the amino-terminal fragment may be blocked in some cases, a viral coat protein can be sequenced by fast atom bombardment (FAB) and mass spectrometer analyses, applying techniques known to those skilled in the art. The amino-acid sequence of the protein can then be compared with the sequence derived by sequencing of the cloned cDNA. A cDNA segment thereby identified as encoding the viral coat protein can be obtained by introducing a new restriction site and ATG translational initiator codon immediately adjacent, vis-a-vis the 5' end, to the codon for the NH$_2$-terminal amino acid of the mature coat protein. This can be done by the method of Zoller & Smith (1982). After restriction enzyme digestion to excise the coat protein coding sequence, the isolated CP coding sequence can be ligated to a suitable promoter, as described above, and placed into plants, in accordance with the present invention, to impart virus resistance.

EXAMPLE 2

Virus Disease Resistance in Transgenic Plants Containing a Virus Coat Protein Gene (Tobacco Mosaic Virus)

This example illustrates how the present invention is practiced when the nucleotide sequence of a virus coat protein gene is available.

A. Preparation of Plasmid pMON319

RNA was removed from tobacco mosaic virus (TMV; common U1 vulgare strain; sequence published by Goelet et al (1982)) by phenol extraction as described in Bruening (1976). A 35-mer oligonucleotide primer was synthesized, complementary to the 3' end of the viral RNA and having, in addition, NdeI and BamHI cleavage sites. The oligonucleotide was annealed to the viral RNA, and served as a primer for the synthesis (using reverse transcriptase) of cDNA, according to the method of Maniatis (1982). The single stranded DNA was converted into double stranded (ds) DNA by the method of Maniatis (1982).

The ds-cDNA was cleaved by BamHI, which cleaves at a site on the primer, and by HindIII, which cleaves at base 5080 of the TMV sequence. The resulting 1.3 kb fragment was mixed with plasmid pUC9 DNA that had also been cleaved with HindIII and BamHI. The resultant ampicillin resistant plasmid, pTM37, was the source of the coat protein coding sequence DNA used for further manipulations, and has an EcoRI site adjacent to the BamHI site.

To obtain a smaller DNA fragment with the coat protein coding sequence, plasmid pTM37 was digested with AhaIII, which cleaves at base 5707 of the TMV sequence (five base pairs from the ATG translational initiation codon for the coat protein mRNA), and with EcoRI, which cleaves just beyond the end of the TMV sequences in pTM37. The resulting fragment, approximately 700 base-pairs (bp) in length, was then transferred and cloned into two other plasmids to add restriction sites to the 5' and 3' ends of the coat protein-encoding fragment. These additions of restriction sites facilitated the construction of further plasmids. Alternately, one may choose to add the restriction sites in other ways, such as by site-directed mutagenesis or by ligation of synthetic DNA linkers. These techniques are all within the skill of the art.

The 700 bp, coat protein-encoding sequence fragment, flanked at the 5' end by a BglII site and at the 3' end by an EcoRI site, was excised from the intermediate plasmid by digestion with BglII and EcoRI. This 700 bp fragment was purified and mixed with DNA of plasmid pMON316 that had also been digested with BglII and EcoRI. Plasmid pMON316 is a derivative of pMON200 (Fraley et al (1985); Rogers et al (1985)) which carries a 330 bp segment of the cauliflower mosaic virus (CaMV) that directs the production of a 35S transcript.

The CaMV35S promoter fragment was isolated from plasmid pOS-1, a derivative of pBR322 carrying the entire genome, as a SalI insert, of the CaMV strain CM4-184 (Howarth et al (1981)). The CM4-184 strain is a naturally occurring deletion mutant of strain CM1841. The nucleotide sequences of the CM1841 (Gardner et al (1981)) and Cabb-S (Franck et al (1980)) strains of CaMV have been published, as have some partial sequences for a different CM4-184 clone (Dudley et al (1982)). The nucleotide sequences of the 35S promoters of all of these strains are very similar. The references to nucleotide numbers ("n . . . ") in the following discussion are those for the sequence of CM1841 disclosed by Gardner et al (1981).

The 35S promoter was isolated from the pOS-1 clone of CM4-184 as an AluI (n 7143)-EcoRI* (n 7517) fragment which was inserted first into pBR322 cleaved with BamHI, then treated with the Klenow fragment of DNA polymerase I and finally cleaved with EcoRI. The promoter fragment was then excised from pBR322 with BamHI and EcoRI, treated with Klenow polymerase and inserted into the SmaI site of M13 mp8 (Messing & Vieira (1982)) so that the EcoRI site of the mp8 multilinker was at the 5' end of the promoter fragment. Site-directed mutagenesis (Zoller & Smith (1982)) was then used to introduce a guanidine residue at nucleotide 7464 to create a BglII site.

Figure 3:
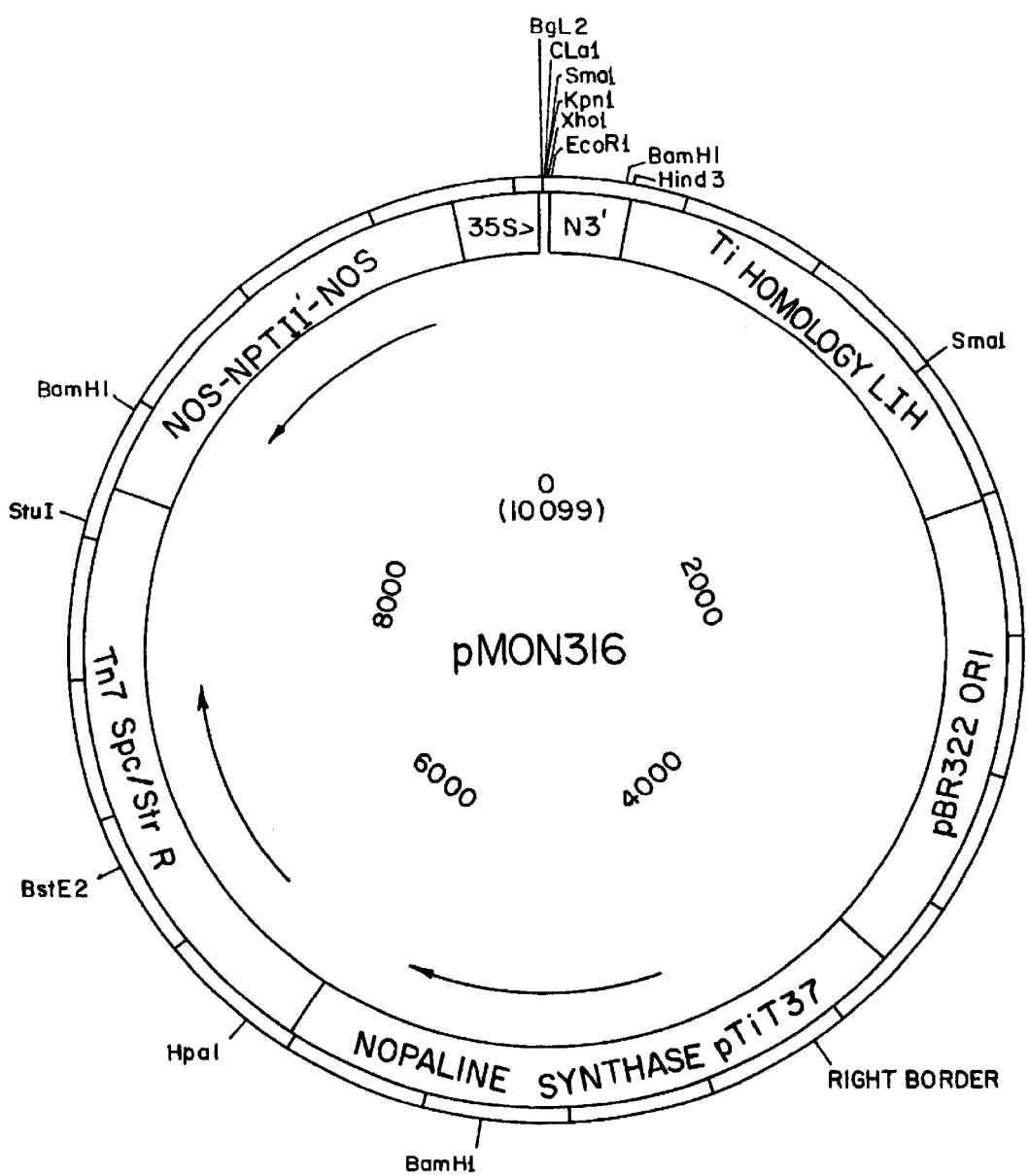
FIG. 3 depicts an expression vector, pMON316, containing the CaMV35S promoter adjacent to a synthetic multilinker containing unique cleavage sites for the restriction endonucleases BglII and EcoRI. The multilinker is followed by a 260 base pair fragment encoding the nopaline synthase gene polyadenylation signals.

The 35S promoter fragment was then excised from the M13 as a 330 bp EcoRI-BglII fragment which contains the 35S promoter, transcription-initiation site and 30 nucleotides of the 5' nontranslated leader, but does not contain any of the CaMv translational initiators or the 35S-transcript polyadenylation signal that is located 180 nucleotides downstream from the start of transcription (Covey et al (1981); Guilley et al (1982)). The 35S promoter fragment was joined to a synthetic multilinker and a 260 bp Sau3A fragment (nucleotides 665–417) of the pTiT37 nopaline synthase gene (Bevan et al (1983)) from the NOS 3' nontranslated region; the segment thus prepared was then inserted into pMON200 to give pMON316 (FIG. 3). The complete sequence of the 35S promoter, multilinker and NOS 3' segment is given in FIG. 4. This sequence begins with an XmnI site created by Klenow polymerase treatment to remove the EcoRI site located at the 5' end of the 35S promoter segment.

Plasmid pMON316 is a cointegrating-type intermediate vector with unique cleavage sites, located between the 5' leader and the NOS polyadenylation signals, for the restriction endonucleases BglII, ClaI, KpnI, XhoI and EcoRI. The cleavage sites permit the insertion of coding sequences carrying their own translation-initiation signals immediately adjacent to the 35S-transcript leader sequence. The pMON316 plasmid retains all of the properties of pMON200, including spectinomycin resistance for selection in E. coli and A. tumefaciens, as well as a chimeric kanamycin gene (NOS-NPTII'-NOS) for selection of transformed plant tissue and the nopaline synthase gene for ready scoring of transformants and inheritance in progeny. The pMON316 plasmid contains the above-described CaMV35S promoter-NOS cassette, which is lacking in pMON200, but is used in substantially the same manner as the latter plasmid (see Fraley et al (1985); Rogers et al (1986)).

Figure 5:
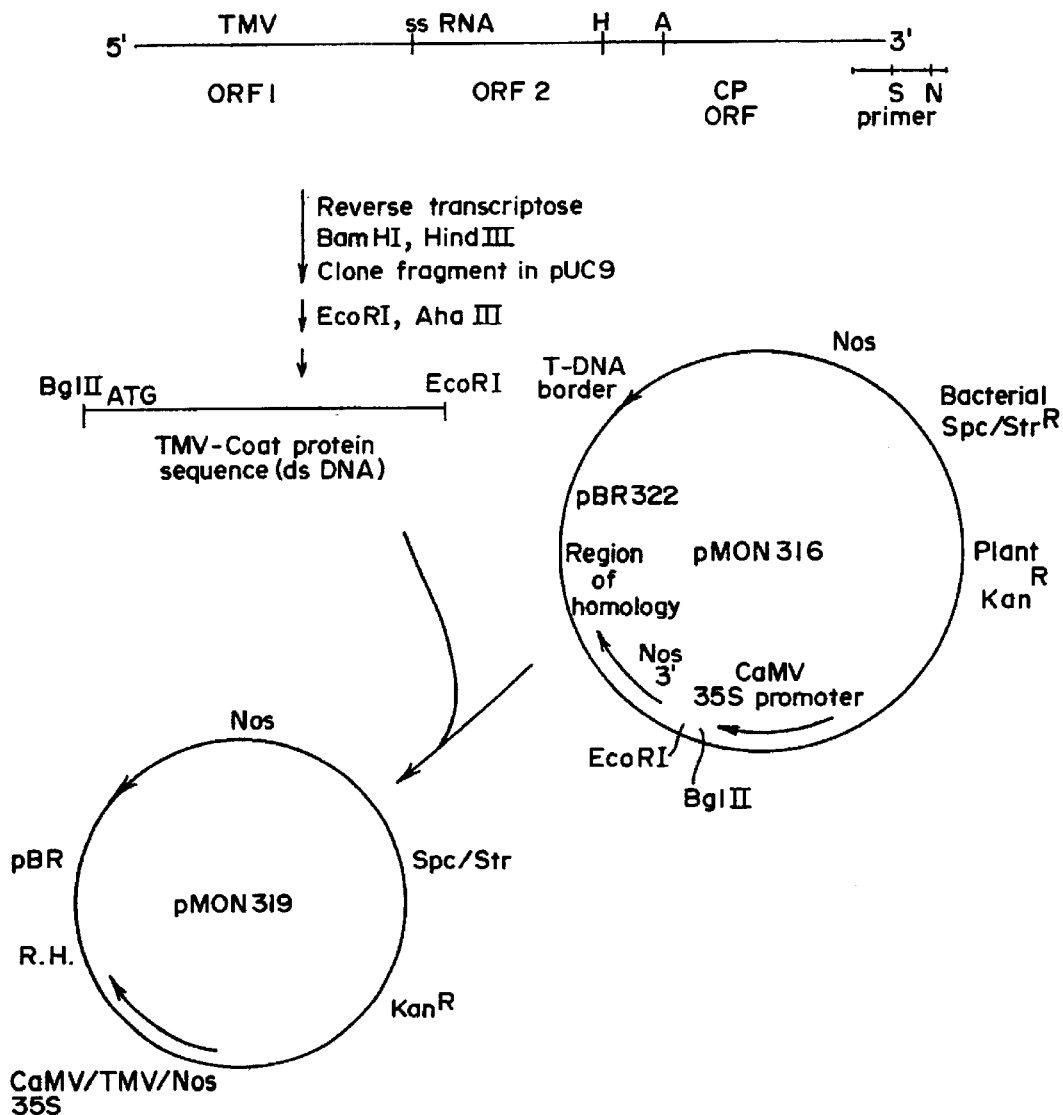
FIG. 5 depicts the plant transformation vector, pMON319, which contains a CaMV35S/TMB-DP/NOS construct. This vector was used to insert the construct into plant cells.

Insertion of the 700 bp TMV coat protein encoding segment provides appropriate signals for the synthesis of this protein in transformed plant cells. The resultant plasmid, designated "pMON319," appears in FIG. 5.

B. Insertion of DNA Construct Containing CP Gene Into Plant Cells

Plasmid pMON319 was inserted, pursuant to Fraley et al (1985), into A. tumefaciens cells containing a disarmed Ti plasmid designated "pTiB6S3-SE." This plasmid does not contain a fully functional T-DNA region; it contains a left T-DNA border.

The pMON319 plasmid carries a marker gene, which conveys selectable resistance to spectinomycin (Spc) and streptomycin (Str) in bacteria, and a region of homology which can cause a crossover event to combine pMON319 with pTiB6S3-SE, thereby creating co-integrate Ti plasmids which have reconstituted T-DNA regions containing the CaMV35S/TMV-CP/NOS construct. However, pMON319 cannot replicate independently in A. tumefaciens cells. Therefore, in the presence of Spc and Str, the only A. tumefaciens cells which can survive are those cells that have cointegrate plasmids.

A culture of A. tumefaciens containing the cointegrate Ti plasmid was contacted with leaf disks taken from tobacco plants (Nicotiana tobacum cv. "Samsun") as described by Horsch et al (1985). The Agrobacterium cells inserted the DNA constructs into the chromosomes of the plant cells. Plant cells resistant to kanamycin were selected and regenerated into differentiated plants by the procedure described in Horsch et al (1985).

The plants which served as experimental controls contained either (1) no foreign genes or (2) only the pMON200 plasmid.

A culture of A. tumefaciens cells containing the pMON319::pTiB6S3-SE cointegrate plasmid was deposited with the ATCC in accordance with the Budapest Treaty, and was assigned accession number 53294.

C. Expression of Viral RNA in Plant Cells

RNA was extracted from leaves of regenerated plants by the method of Lane & Tremiates-Kennedy (1981). RNA's were separated according to size by electrophoresis in agarose gels containing formaldehyde and blotted to nitrocellulose, as described in Maniatis et al (1982). Viral RNA was detected on the nitrocellulose by the hybridization to the $^{32}$P-labeled DNA clone using methods described in Maniatis et al (1982).

Based on this RNA hybrization analysis, it was determined that transformed plants (those carrying pMON319) contained viral RNA, while plants which contained only pMON200 did not contain viral RNA. The presence of TMV coat protein was detected in plants containing pMON319 but not pMON200. Proteins were extracted from leaves by grinding in sample buffer, following Laemmli (1970). A 50/ug portion of protein was subjected to electrophoresis in 12% polyacrylamide gels containing SDS, as disclosed by Laemmli (1970). Proteins were electrophoretically transferred to nitrocellulose, as disclosed by Towbin et al (1979).

Blotted proteins were reacted with antiserum raised in rabbits against purified TMV, as disclosed by Symington et al (1981). Rabbit antibodies bound to the TMV on the nitrocellulose were detected by binding with $^{125}$I-labeled donkey anti-rabbit antiserum (Amersham Co., Chicago).

Based on the results of the immunoblot analysis, it was determined that transformed plants (containing pMON319) produced TMV coat protein, whereas plants containing only pMON200 did not produce TMV coat protein. The amount of coat protein produced in these leaves was about 50 nanograms of coat protein in 50/ug of total leaf protein, or 0.1%.

D. Resistance of Tobacco Plants to TMV

The transformed and control plants were grown to a height of about two feet, and then were divided into cuttings of stem sections, with axillary buds, which were rooted and regenerated into individual plants. These plants were inoculated with TMV by adding abrasive particles to an aqueous suspension of the virus particles, and rubbing the abrasive solution on the leaves. More specifically, TMV was suspended in 0.05M sodium phosphate buffer (pH 7.2). Approximately 50/ul of solution was applied, by rubbing, to tobacco leaves that had been dusted with carborundum (320 Grit, manufactured by Fisher Scientific Co.). After the leaf surface had dried, leaves were rinsed with water and plants were placed in a greenhouse, or growth chamber.

Control plants displayed symptoms of infection within about three to five days after inoculation. In contrast, the plants that contained the DNA construct of the present invention did not produce symptoms until from eight to ten days after inoculation. These results were confirmed in three independent sets of experiments.

In another experiment, seeds produced by two different transformed plants containing pMON319 were germinated, and the seedlings were grown in soil. Each seedling was assayed for the presence or absence of TMV coat protein by the immunoblotting technique described above. A total of 39 seedlings were inoculated as previously described with a suspension containing TMV (0.25/ug/ml) in a blind fashion, i.e., without prior knowledge of whether the seedling contained TMV coat protein. Experimental results indicated that 11/39 plants contained coat protein; the remainder did not contain coat protein, and served as a control for this experiment.

Five days after inoculation 3/11 (27%) of control plants produced typical symptoms of TMV infection. None of the plants containing TMV coat protein showed such symptoms.

Six days after inoculation 45% of control plants produced typical symptoms of TMV infection. Whereas only 18% of the plants containing TMV coat protein showed such symptoms.

Seven days after inoculation 82% of control plants produced typical symptoms of TMV infection. 57% of the plants containing TMV coat protein showed such symptoms.

Eight days after inoculation 82% of control plants had produced symptoms typical of TMV infection. 64% of the plants containing TMV coat protein showed such symptoms.

The observation of a substantial delay in the onset of symptoms in the face of a massive assault by the virus is an indication that the transformed plants are substantially more resistant to the virus than the untransformed plants. The extent of the increased resistance observed in these experiments indicates that the transformed plants are capable of withstanding the type of infective contact that is likely to occur in an open field or in a greenhouse.

EXAMPLE 3

Characterization of Virus Disease Resistance in Transgenic Plants

A. Dose-Response in Tobacco

Figure 6:
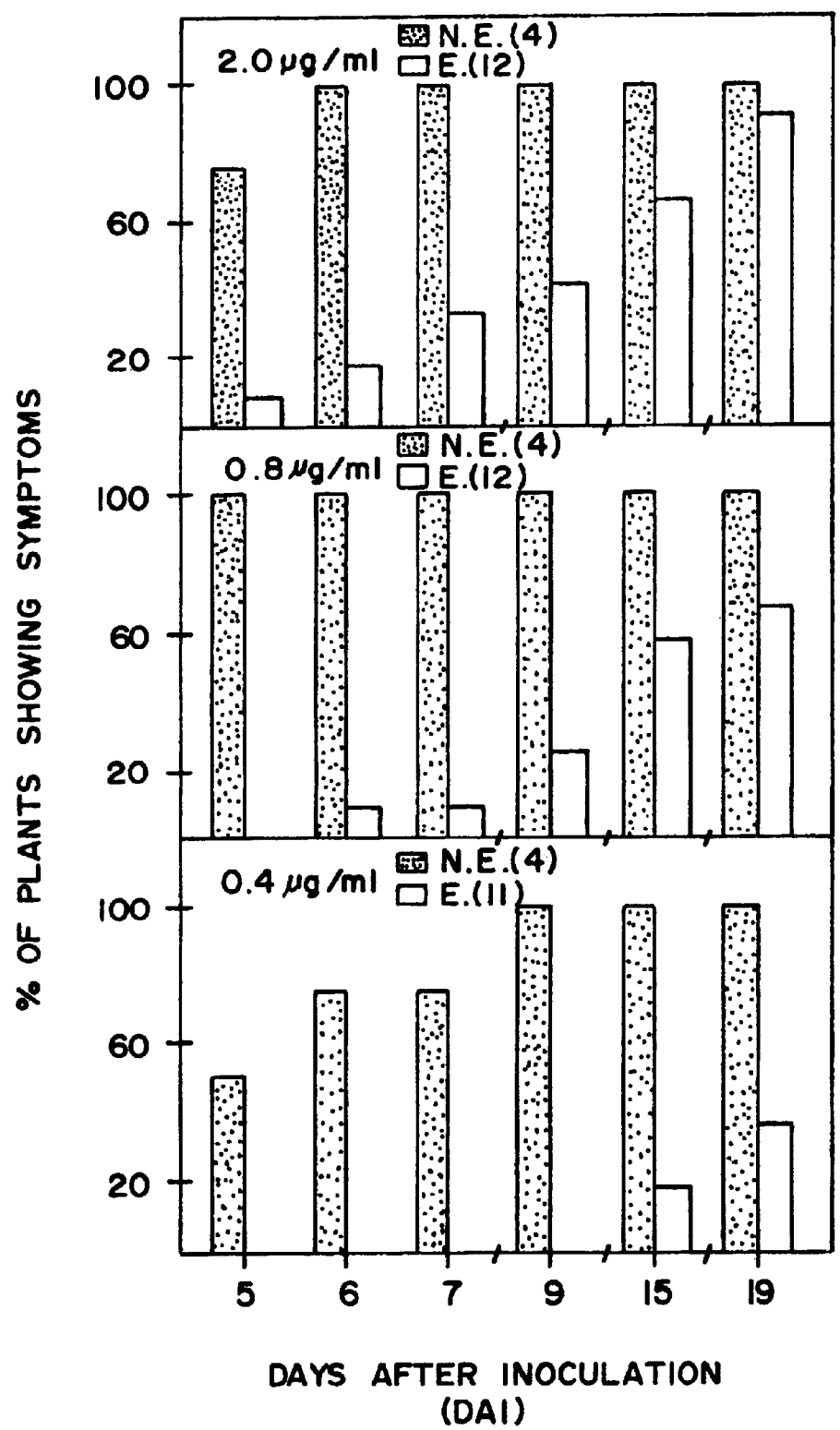
FIGS. 6 and 7 represent, respectively, data from experiments, described in Examples 3(A) and 3(B), involving the effect of differing levels of viral exposure on transgenic tobacco and tomato plants produced, respectively, in accordance with the present invention.

Seedlings of transformed tobacco plants described in Example 2 were used for these experiments. Plants that were determined to express the CP coding sequence, or not to express the CP coding sequence, by the immunoblot techniques described above were divided into three groups and inoculated with a suspension containing TMV (U1 vulgare strain) as previously described. The three groups were inoculated with suspensions containing TMV at concentrations of 0.4/ug/ml, 0.8/ug/ml and 2.0/ug/ml, respectively. The inoculated plants were put into a greenhouse and observed for symptoms of virus infection. The bar graph of FIG. 6 represents the results of this experiment. The data clearly show that the plants expressing the coat protein were quite resistant to the virus at ~0.4/ug/ml or less.

B. Dose-Response in Tomato

A culture of *A. tumefaciens* cells containing the cointegrate plasmid pMON319::pTiB6S3-SE were contacted with leaf disks taken from tomato plants, again using the method described in Example 2. Kanamycin-resistant tissue containing the CaMV35S/TMV-CP/NOS construct was selected and regenerated into plants. The test plants were seedling progeny of the self-fertilized transgenic tomato plants. The control plants for this experiment were untransformed parental plants and non-expressing seedling progeny.

Figure 7:
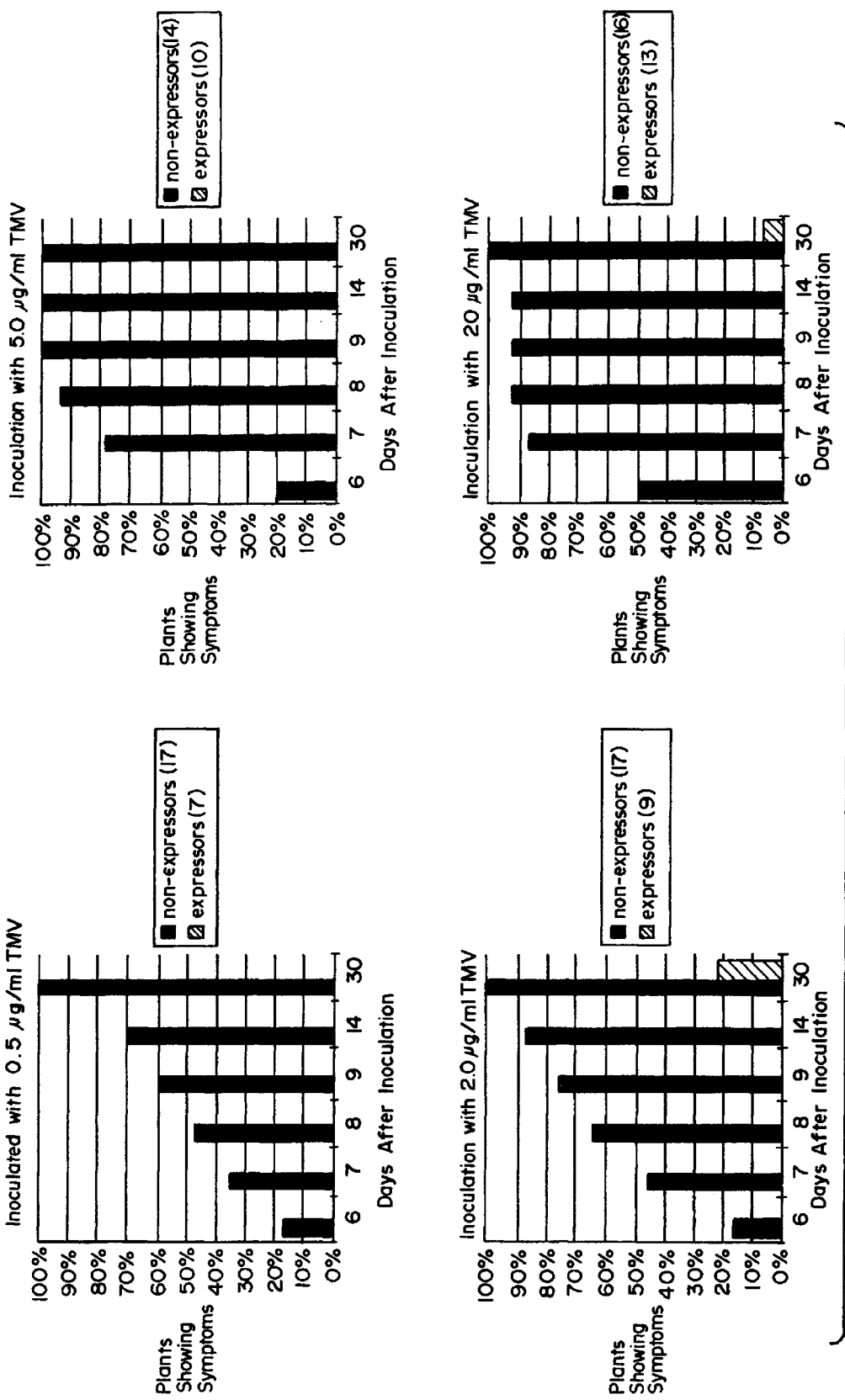

Test and control plants were inoculated with a suspension containing TMV at concentrations between 0.5/ug/ml and 20/ug/ml following the inoculation method of Example 2. The results of this experiment are shown in FIG. 7. As shown in FIG. 7, all control plants exhibited symptoms of viral infection within the thirty-day period. In addition, control plants exhibited a more immediate display of symptoms with increased viral inoculum. In contrast, seedlings expressing the TMV coat protein were substantially resistant to TMV infection and did not develop symptoms of infection until 30 days post-inoculation, if at all.

C. Comparison with Genetic Resistance

To characterize further the resistance imparted to the above-described seedling progeny in accordance with the present invention, the response to ToMV inoculation of tomato plants known to contain a genetic determinant for ToMV resistance was compared to the corresponding response of transgenic plants prepared using the method of Example 2. More specifically, plants of the variety "Craigella," into which the resistance determinants Tm-2 or Tm-2a, respectively, had been introduced by conventional breeding techniques, were inoculated with a ToMV strain designated "ToMV2" or "ToMV2a." (Data bearing on the relative sensitivities of plants carrying different resistance determinants to ToMV infection by various strains, including ToMV2 and 2a, are indicated in a table below.) A test group comprising transgenic plants of an otherwise ToMV2-sensitive variety ("VF36"), which plants were transformed and expressed TMV coat protein, was also inoculated with the same virus strains, as was a control group of untransformed VF36 plants.

| Plant Groups | TMV* | ToMV Strains 2 | 2a |
|---|---|---|---|
| VF36 | 5/5 | 5/5 | 5/5 |
| Tm-1 | 0/5 | 0/5 | 0/5 |
| Tm-2 | 0/5 | 5/5 | 0/5 |
| Tm-2a | 0/5 | 0/5 | 3/5 |
| Transgenic | 1/5 | 3/5 | 1/5 |

\* = TMV strain PV230
+ = Susceptible
− = Resistant

Figure 8:
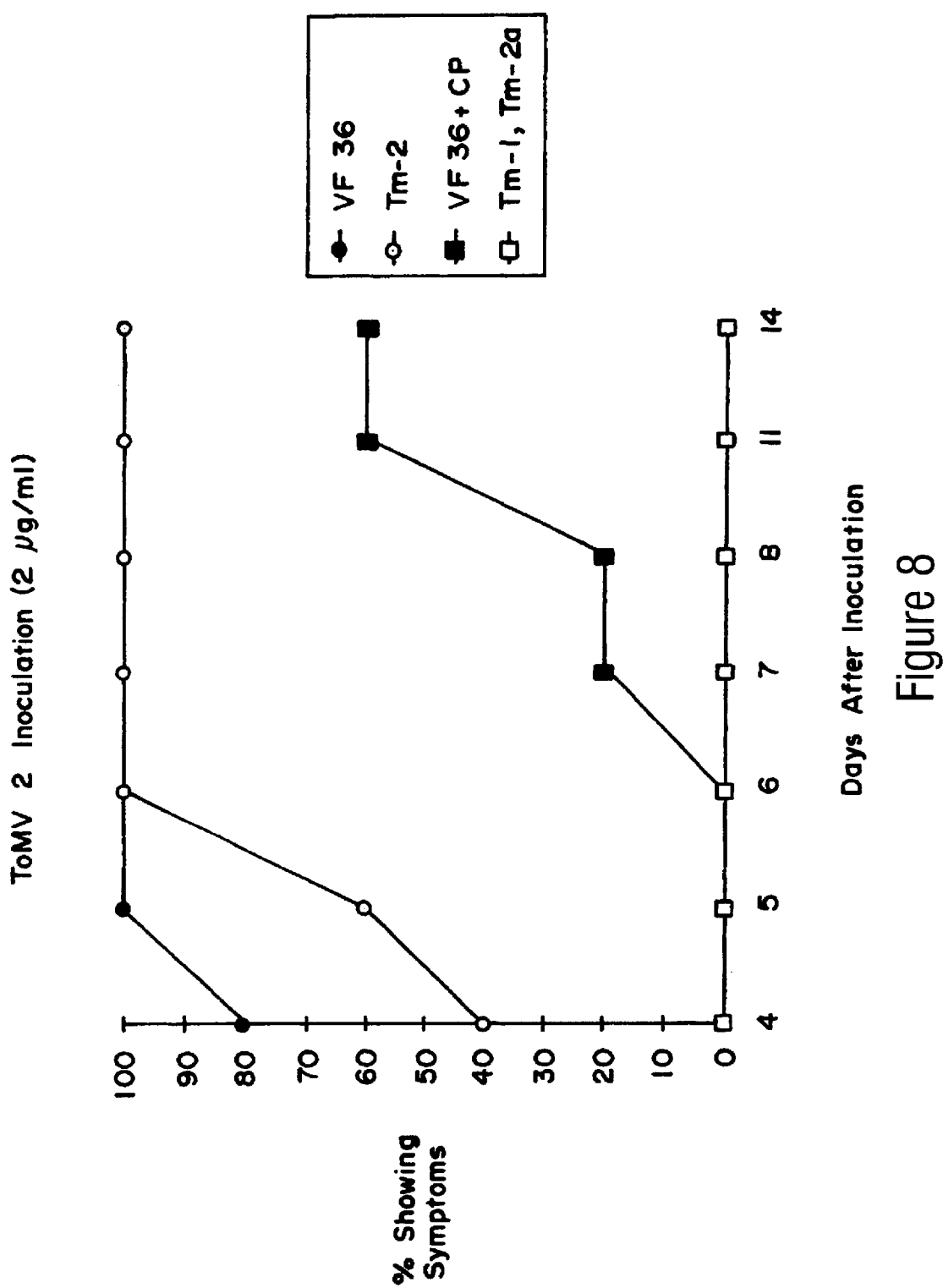
FIG. 8 represents the data from an experiment, described in Example 3(C), involving comparisons of virus resistance between tomato plants from genetically-resistant lines and transgenic plants produced according to the present invention.

Five plants in each group were scored for disease symptoms 14 days after inoculation. Within 14 days post-inoculation, both the control plants and the plants containing the Tm-2 determinant all developed symptoms of ToMV2 infection; three of five transgenic plants displayed symptoms over the same period (see FIG. 8). The data in the foregoing table demonstrate that transgenic plants exhibit a level of resistance that is substantially better than the nontransformed controls and, moreover, is nonselective against multiple strains of ToMV (see also FIG. 8). In contrast, genetic resistance is considerably narrower in scope. Among the test plants, 60% eventually did show signs of infection, but the symptoms were less severe than those of the Tm-2 plants. These results indicate that the resistance to ToMV2 imparted by CP expression in the test plants was comparable, if not better than, the genetic resistance encoded by Tm-2.

EXAMPLE 4

Cross-Protection Against Different Strains of Tobacco Mosaic Virus

Transformed tomato plants carrying the CaMV35S/TMV-CP/NOS construct were prepared in the manner described in Example 3. Seedling progeny of self-fertilized transgenic tomato plants were the test plants for this experiment. Control plants were seedling progeny not expressing the TMV coat protein and normal untransformed plants of the parental type.

Test and control plants were inoculated with two different strains of TMV:

PV-230—A virulent strain of TMV obtained from the ATCC (accession No. PV-230).

L-TMV—A strain known to infect tomato plants.

Figure 9:
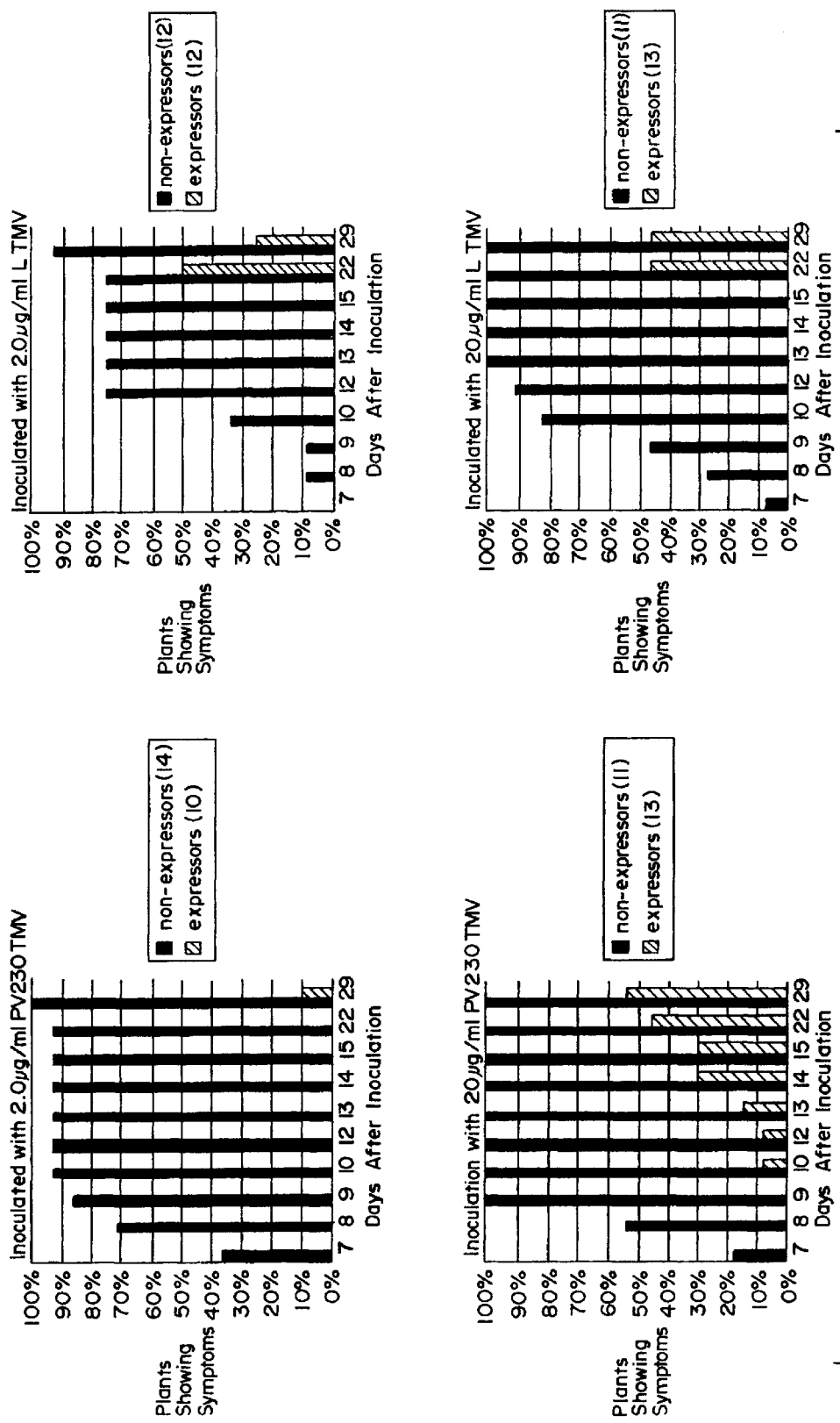
FIG. 9 represents the data from an experiment, described in Example 4, involving the induction of cross-protection in tomato plants, pursuant to the present invention, which was effective against different strains of tobacco mosaic virus.

Test and control plants were inoculated with each of the foregoing TMV strains, at concentrations of 2/ug/ml and 20/ug/ml, respectively, following the method described in Example 2. The results of this experiment are shown in FIG. 9. The data clearly show that the transgenic tomato plants which expressed TMV coat protein were resistant to TMV infection. Resistance was exhibited against both strains of TMV tested. Moreover, a higher percentage of tomato plants (from 40% to 100%) did not develop symptoms within 29 days after inoculation despite the use of the virulent strain PV-230 at a concentration as high as 20/ug/ml.

EXAMPLE 5

Control of Virus Coat Protein Gene by Different Promoters

An experiment was conducted to demonstrate the use of other promoters in the present invention and to demonstrate the correlation between the level of expression of coat protein and virus resistance.

Group I plants were seedling progeny of transgenic tobacco plants transformed to carry the CaMV35S/TMV-CP/NOS construct as described in Example 2.

Group II and III plants were seedling progeny of transgenic tobacco plants transformed to express the TMV coat protein gene, as were Group I plants, except that a ssRUBISCO promoter from petunia (Tumer et al (1986)) was substituted for the CaMV35S promoter by the following procedure.

Figure 10:
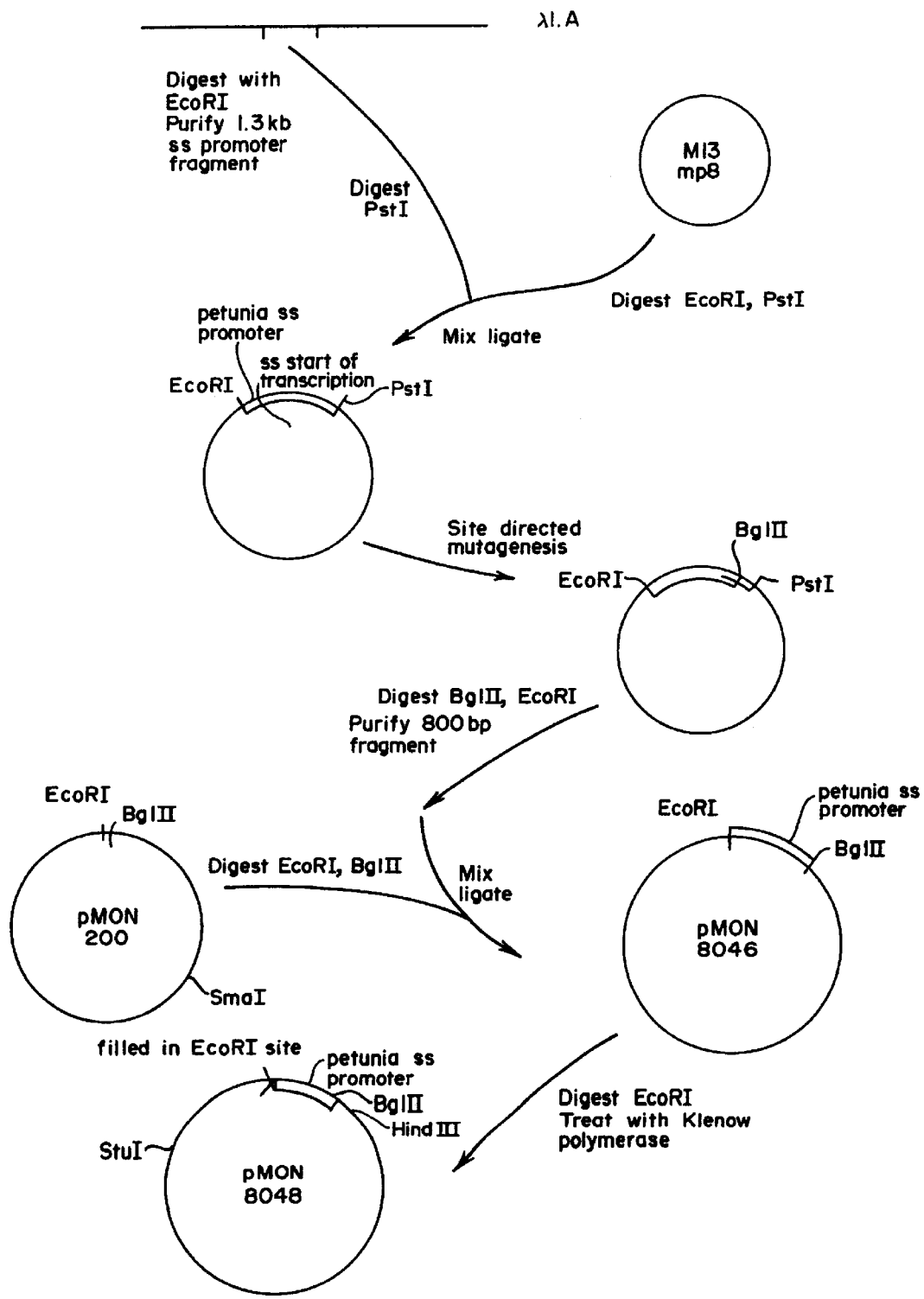
FIG. 10 depicts the initial isolation and incorporation into an intermediate vector of the ssRUBISCO promoter from petunia which was used in Example 5.
Figure 11:
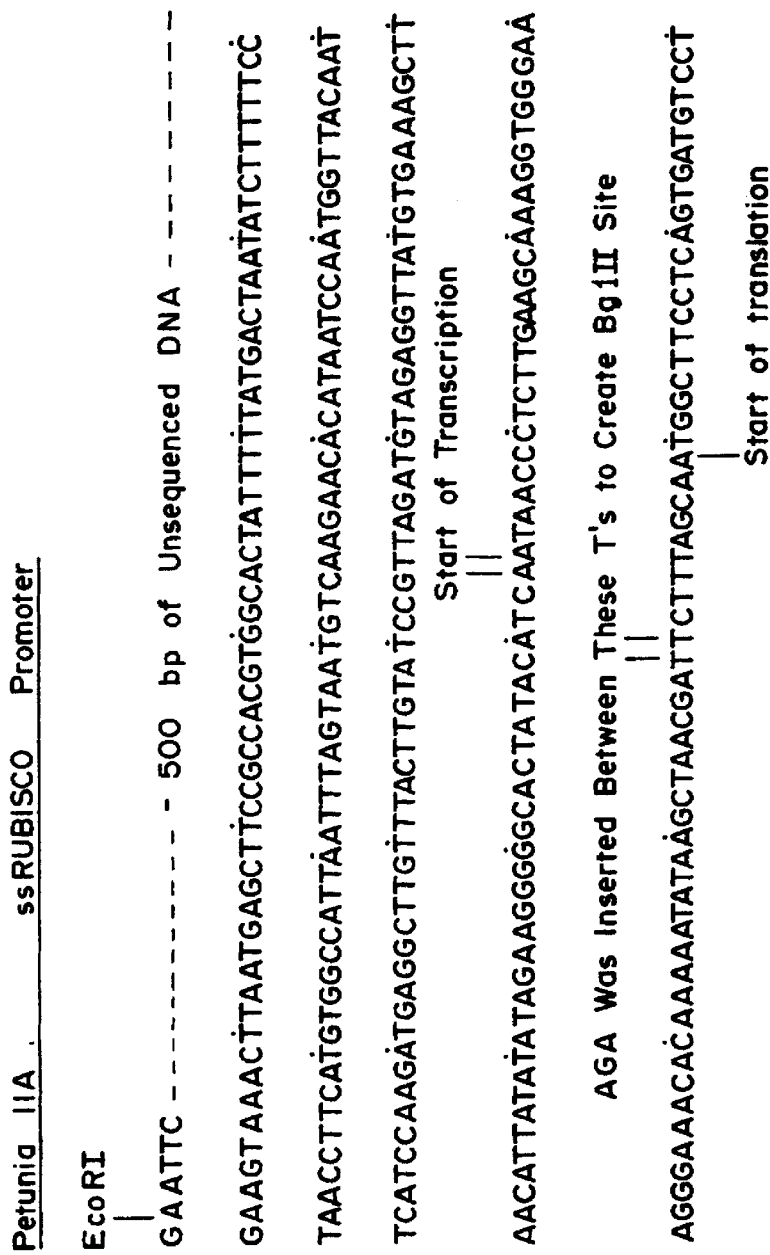
FIG. 11 represents a partial nucleotide sequence of the ssRUBISCO promoter of petunia used in Example 5.

The petunia 11A small subunit (ss) promoter fragment was isolated, via cleavage with EcoRI, from a genomic clone carried in bacteriophage lambda (Tumer et al (1986)). A resulting 1.3 kb EcoRI fragment that carries the promoter was further digested with PstI and inserted between the PstI and EcoRI sites of phage M13mp8 for site-directed mutagenesis to introduce a BglII site into the 5' non-translated sequence of the small subunit transcript (FIG. 10). A partial sequence of the petunia 11A ss promoter and the mutagenesis primer appear in FIG. 11. After cleavage with EcoRI and BglII, the resulting 800 bp fragment was inserted into pMON200 that had been cleaved with EcoRI and BglII. The resulting plasmid pMON8046 was digested with EcoRI, treated with the large Klenow fragment of DNA polymerase and with DNA ligase. A plasmid that had lost the EcoRI site was isolated and named pMON8048 (see FIG. 10).

Figure 12:
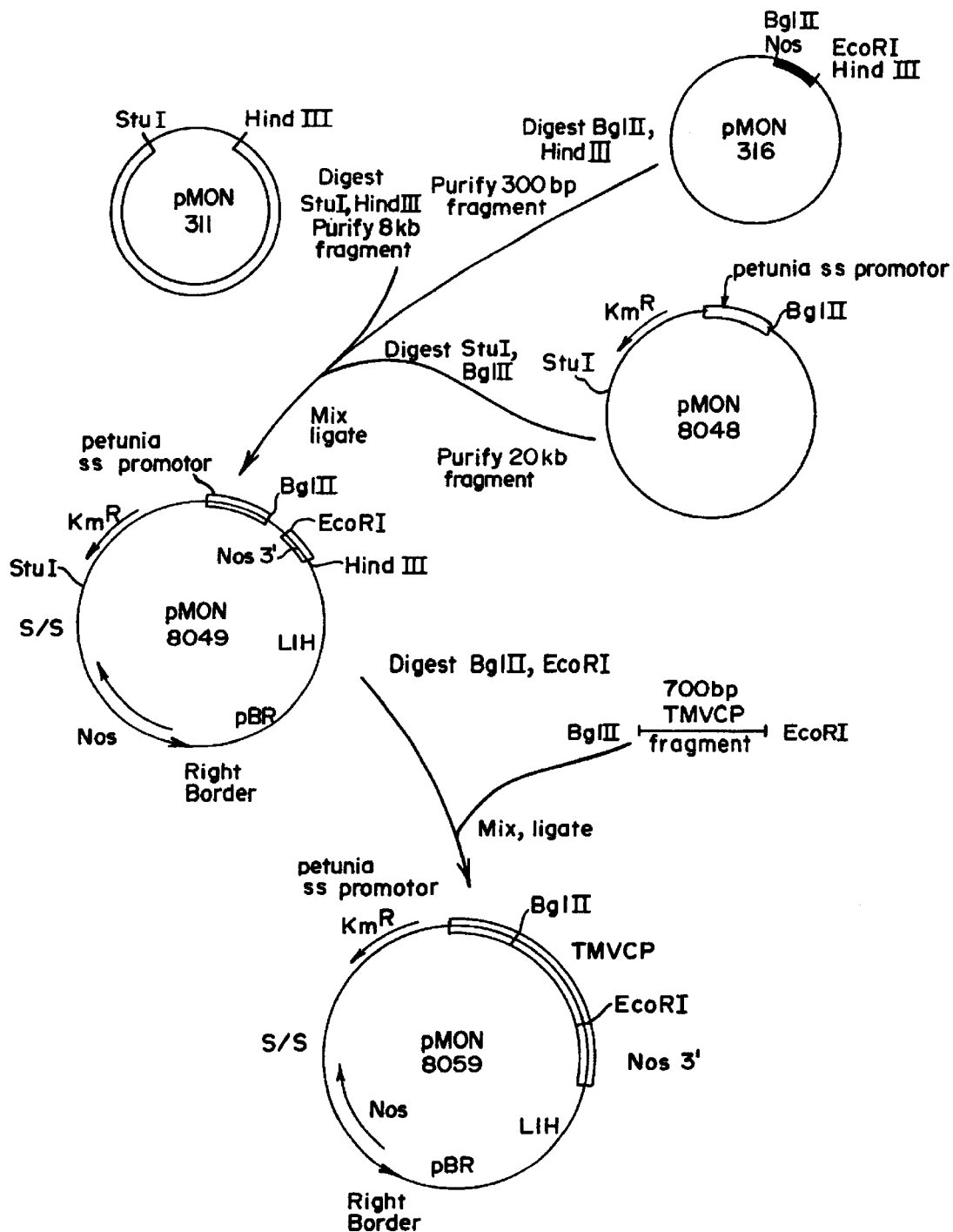
FIG. 12 outlines the production of a DNA construct wherein the CaMV35S promoter is replaced by the ssRUBISCO promoter of petunia.

To construct a petunia ss-NOS 3' cassette, plasmid pMON311, a derivative of pMON200 wherein the SmaI site had been replaced with a BamHI linker from which the BamHI site was then removed by treatment with Klenow polymerase and ligase, was digested with StuI and HindIII. The resulting 8 kb fragment was then mixed with the 300 bp BglII-to-HindIII fragment purified from pMON316 and the 2.6 kb StuI-to-BglII fragment of pMON8048. The resulting plasmid pMON8049 is similar to pMON316 except that the CaMV35S promoter has been replaced by the petunia ss promoter (FIG. 12). The above-described, 700-bp TmV-CP coding sequence fragment, containing a BglII site at the 5' end and an EcoRI site at the 3' end, was inserted into pMON8049 that was cleaved with BglII and EcoRI to yield pMON8059 (see FIG. 12), which carries a petunia ss promoter/TMV-CP/NOS construct.

Group IV plants were transformed to contain only plasmid pMON200, and served as control plants.

Each group contained 30 plants that were inoculated with TMV following the procedure outlined in Example 2(D). After inoculation, the plants were placed in the greenhouse and observed for symptoms of virus infection.

The relative levels of TMV coat protein were estimated by Western blot analysis. With the mean value for the extent of coat protein gene expression in Group I plants valued at 100%, the following determinations were made:

| Mean Value of CP Expression | |
|---|---|
| Group I | 100 |
| Group II | 14 |
| Group III | 3 |
| Group IV | 0 |

-continued

| | Percent of Plants Displaying Symptoms (Days Post-Inoculation) | | | | | | |
|---|---|---|---|---|---|---|---|
| Group | 3 | 4 | 5 | 6 | 7 | 8 | 10 |
| I | 0 | 3 | 7 | 23 | 40 | 47 | 50 |
| II | 0 | 3 | 13 | 63 | 83 | 97 | 97 |
| III | 0 | 0 | 15 | 88 | 100 | | |
| IV | 0 | 13 | 70 | 100 | | | |

The data shown above support the following conclusions:
(1) The ribulose bis-phosphate carboxylase small subunit promoter is an effective promoter for use in the present invention, although it may not be as strong a promoter in certain plants as the CaMV35S promoter.
(2) There is a positive correlation between the level of expression of coat protein and viral resistance.

EXAMPLE 6

Virus Disease Resistance in Transgenic Plants Containing a Virus Coat Protein Gene (Alfalfa Mosaic Virus)

A DNA construct comprising the coat protein coding sequence of alfalfa mosaic virus (AMV CP) was prepared employing a strategy similar to that used for engineering TMV resistance. A full-length cDNA clone, encoding the coat protein of AMV, was obtained as described below and outlined in FIG. 13. The AMV coat protein CDNA was fused to the CaMV35S promoter and the NOS 3' end as described previously. The construct can then be transferred to plants using the Agrobacterium-mediated transformation system.

The complete nucleotide sequence of the tripartite RNA genome of AMV is known. The data indicate that the AMV genome encodes four primary gene products: A 126 kilodalton (kd) protein encoded by RNA 1, a 90 kd protein encoded by RNA 2 and a 32 kd protein encoded by RNA 3. The coat protein is translated from a subgenomic messenger, designated "RNA 4," which is homologous to the 3' terminal 881 nucleotides of RNA 3 (Barker et al (1983b)).

To synthesize a full-length cDNA encoding the coat protein of AMV, synthetic oligonucleotide primers for both first- and second-strand CDNA synthesis were used. With reference to FIG. 13, the primers used included unique EcoRI sites at each end of the AMV coat protein coding sequences. First-strand cDNA was synthesized from 5/ug AMV total RNA and 55 ng primer in a 100/ul reaction using 4 mM sodium pyrophosphate and reverse transcriptase. By this method, cDNA's were synthesized that were $1.04 \times 10^6$ (RNA 1), $0.73 \times 10^6$ (RNA 2) and $0.68 \times 10^6$ (RNA 3) daltons in molecular weight. After the RNA template was hydrolyzed, the cDNA products were fractionated on a P-60 column. The single-stranded cDNA was annealed to the second-strand primer and incubated with reverse transcriptase. The resulting double-stranded cDNA contained AMV coat protein sequences flanked by EcoRI sites at each end. After digestion with EcoRI, the cDNA's were inserted into the EcoRI site of pUC9, and *E. coli* JM101 cells were transformed and selected on media containing ampicillin, IPTG and X-Gal. Approximately 1000 transformants were obtained. Twenty-five percent of the transformants hybridized to both the 5' and 3' specific primers. DNA was prepared from three positives, and an EcoRI digest revealed the presence of inserts with the expected size (881 bp). It was confirmed by nucleotide sequencing (~100 bp on each end) that these clones did, in fact, contain full-length AMV coat protein inserts.

The 881 bp EcoRI fragment encoding the AMV coat protein was incorporated into the plant expression vector pMON316 in sense and antisense orientations (pMON9800 and pMON9801, respectively). The structure of pMON9800 is shown in FIG. 13. These vectors were then transferred to tobacco, tomato and petunia using the Agrobacterium-mediated transformation system described in Example 2.

To investigate further the expression of the AMV coat protein mpNA, Northern blot analysis was performed on callus tissue from transgenic tobacco plants (cv. "Samsun") containing the AMV coat protein gene in sense orientation (pMON9800). Total RNA (40/ug) from pMON9800 and pMON273, a vector control derived from pMON200 which lacks the AMV CP coding sequence, was loaded onto an agarose gel, was transferred to a membrane (Gene Screen®, manufactured by New England Nuclear), and then was probed with the 881-bp cDNA insert which coded for the AMV coat protein. A group of bands which corresponded to the expected size of the transcript (1.2 kb) showed very strong hybridization. There were also transcripts of smaller size which hybridized to the probe. No hybridization to the control callus, which was transformed with pMON273, was detected.

A Western blot protocol was also developed for the detection of AMV coat protein in transgenic and infected plants. A commercially available anti-AMV IgG fraction (Agdia Inc., Mishawaka, Ind.) was used successfully in detecting the coat protein in transgenic tobacco calli and leaves, and in transgenic tomato leaves. More specifically, 30/ug of protein from control and transgenic tobacco calli, and 40/ug of protein from control and transgenic tomato material, were applied to a Western blot, resulting in an immunoreactive band around 28–29 kd molecular weight which comigrated with purified AMV coat protein standard.

Transgenic tobacco plants that were identified as expressing the AMV coat protein were inoculated with AMV. Also inoculated were control plants that either were not transformed or were transformed with vector pMON316. Symptom development was monitored daily in the growth chamber. The control and transgenic plants used were similar in size, physical appearance and developmental stage (all were starting to flower). Three leaves from the control and the transgenic plants, respectively, were inoculated with an extract from AMV-infected plants. Subsequent titration analysis showed that the concentration of the AMV used in this inoculum was approximately 50/ug/ml.

The inoculated leaves of the control transgenic tobacco plants and the nontransformed tobacco plants showed symptoms a week after infection with AMV. In contrast, none of the CP-expressing transgenic plants showed symptoms within a week after infection; after ten days, one of the latter plants had one or two lesions on one of the three inoculated leaves. Two weeks after infection, the number of lesions in the inoculated leaves of the control plants remained the same, but noninoculated upper leaves showed symptoms (chlorotic rings) which were uniformly spread over the surface of the leaves. The transgenic test plants that produced AMV coat protein showed no (or no additional) symptoms on either the inoculated or the systemic (noninoculated) leaves.

Replication of AMV in the transgenic and control plants was determined by monitoring the level of coat protein via Western and dot blot analyses. A week after infection, only background levels of expression were detected by Western blotting in the transgenic plants, i.e., the level of expression detected was comparable to the endogenous level of expression of the introduced coat protein coding sequence. On the other hand, the control plants contained substantially higher levels of AMV coat protein. Quantitation of the hybridization signals by densitometric scanning indicated a 211-fold difference between the transgenic and the nontransformed control tobacco plants. The transgenic tobacco controls were characterized by levels of AMV coat protein that ranged between 110 and 815 times higher than the levels of the AMV transformants. These results indicate that AMV replication is substantially lower in transgenic plants that make the protein.

EXAMPLE 7

DNA Construct Containing Potato Virus X Coat Protein Coding Sequence

A construct comprising the coat protein coding sequence of potato virus X (PVX CP) was prepared employing a process similar to that used for engineering TMV and AMV constructs. Potato virus X (PVX), which belongs to the potexvirus group, contains a single infectious genomic RNA of $2 \times 10^6$ daltons. The 3'-end region of the PVX RNA has been cloned and sequenced. This region contains the coat protein gene, which codes for a protein that is 237 amino acid residues in length (Zakharyev et al (1984)).

A cDNA copy containing the PVX coat protein gene, save for the first ten codons from the 5' end, was synthesized from polyadenylated PVX viral RNA. The cDNA copy, designated "clone p3a," was cloned into the PstI site of pBR322 via the dG.dC tailing method of Zakharyev et al (1984). To repair the 5' end of the gene, a synthetic BamHI-PstI fragment containing 18 bases of authentic 5' non-coding sequence immediately before, and 22 codons after, the initiation codon ATG was used to replace the smaller PstI-PstI fragment that contained the dG.dC tail and 11th–22nd codons. The dG.dC tail and part of dA.dT stretch at the 3' end of the gene were removed by Bal31 digestion of the larger HpaII-PstI fragment subcloned in pUC18, and a ClaI site was created by linker addition. The XhoI-ClaI fragment (approximately 170 bp) was used to replace the XhoI-ClaI fragment which contained, respectively, the original 3' end sequence from p3a and PstI-ClaI sequence from pBR322.

Figure 14:
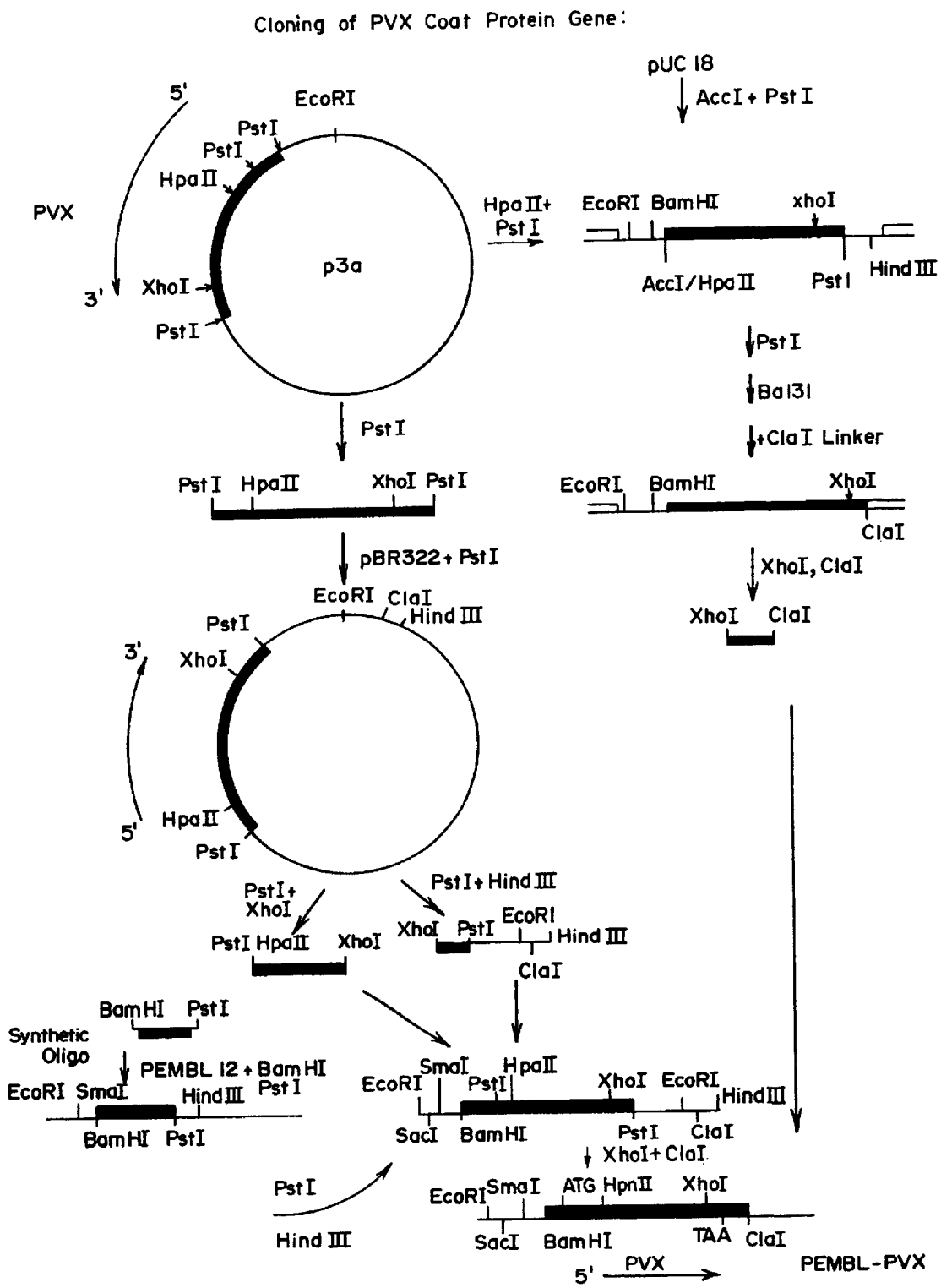
FIG. 14 represents a process used to prepare a plant vector containing the coat protein gene of potato virus X (PVX CP).
Figure 15:
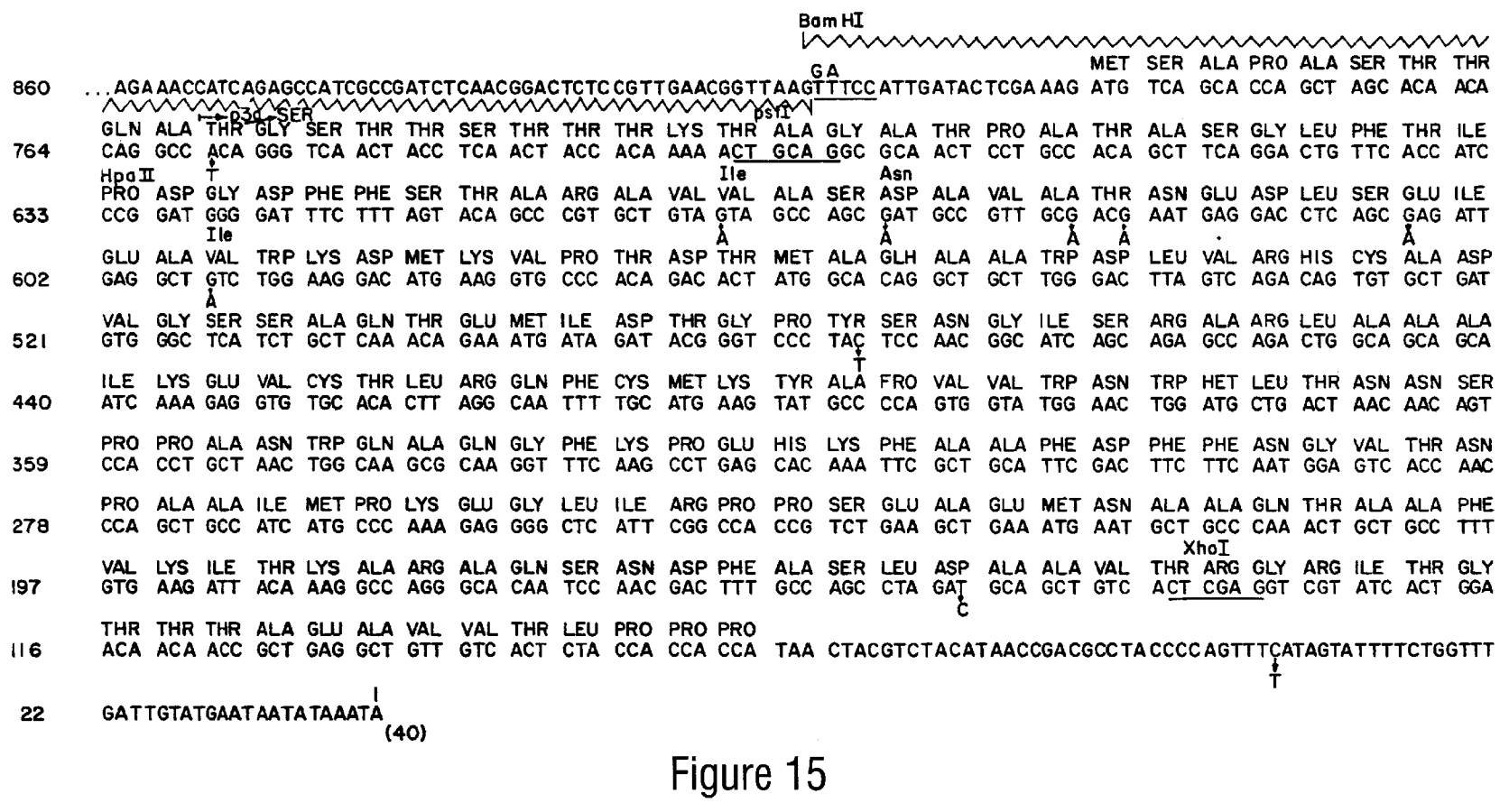

The final construct contained the cDNA of 18 bp of 5' non-coding region, 657 bp of coding region of the coat protein sequence (including TAA, the translation termination codon), 72 bp of 3' non-coding region and 40 bp of dA.dT stretch in pEMBL12(+) (see FIG. 14). The sequence of the PVX coat protein gene is shown in FIG. 15. A horizontal arrow indicates the 5' boundary of the PVX sequence in p3a. The region derived from synthetic DNA is marked with a wavy line above the sequence. Restriction sites used in construction are underlined. Differences between the present sequencing data and that published by Zakharyev et al (1984) are indicated underneath the sequence, and the new amino acids encoded are shown above the original ones.

The full-length cDNA of the PVX coat protein gene was inserted, in both orientations, into expression vectors derived from pMON505, utilizing either the CaMV35S promoter (pMON9818) or the ssRUBISCO promoter (pMON9819) and the rbcS-E9 3' end (Odell et al (1985)). The following vectors were made to express the PVX coat protein gene, and they were transferred to tobacco plants using the Agrobacterium-mediated transformation system described in Example 2:

(a) pMON9809—PVX coat protein coding sequence was inserted into pMON9818 between the CaMV35S promoter and rbcS-E9 3' end in sense orientation.

(b) pMON9810—PVX coat protein cDNA was inserted into pMON9818 between the CaMV35S promoter and rbcS-E9 3' end in antisense orientation.

(c) pMON9811—A 5' fragment of the PVX coat protein coding sequence was inserted into pMON9818 in sense orientation.

(d) pMON9812—A 5' fragment of the PVX coat protein coding sequence was inserted into pMON9818 in antisense orientation.

(e) pMON9813—PVX coat protein coding sequence was inserted into pMON9819 between the rbcS8B promoter and E9 3' end in sense orientation. The plants can be inoculated with PVX and the level of virus resistance determined, as described above.

Unlike mRNA of AMV, potex viral RNA's are polyadenylated, which makes possible an alternative approach to cDNA synthesis by using oligo dT as a primer for first-strand synthesis and DNA polymerase or avian myoblastosis virus reverse transcriptase for the second-strand synthesis. The double-stranded DNA can be manipulated for isolation and expression in plants of the coat protein sequence as detailed earlier in this example.

EXAMPLE 8

Figure 16:
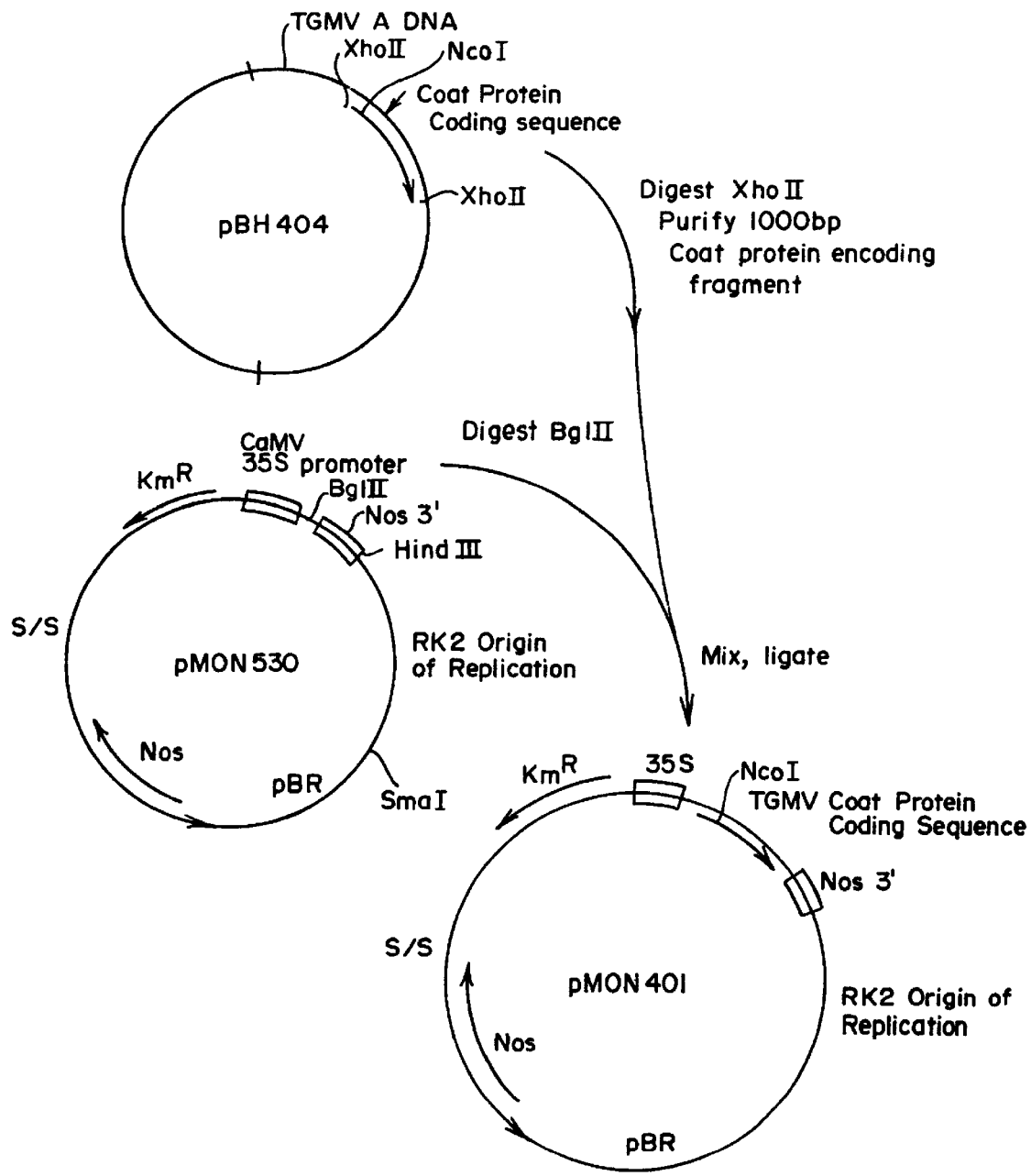
FIG. 16 represents the steps followed to isolate a nucleotide fragment encoding tomato golden mosaic virus coat protein (TGMV CP).

DNA Construct Containing Tomato Golden Mosaic Virus Coat Protein Coding Sequence A plasmid that comprised a DNA construct containing a coding sequence capable of causing the production of the mRNA for the tomato golden mosaic virus (TGMV) coat protein was constructed as follows. Plasmid pBH404 (Bisaro et al (1982)) was digested with XhoII, and the fragment of approximately 1 kb extending from nucleotide 312 to 1285 (Hamilton et al (1984)), which carries the coding sequence of the TGMV coat protein (TGMV CP), was isolated (see FIG. 16). The fragment was inserted into pMON530, which plasmid was constructed by cleavage of pMON200 with NdeI to remove a 900 bp NdeI fragment. This resulted in pMON503, which was cleaved with HindIII and SmaI and mixed with pTJS75 (Schmidhauser & Helinski (1985)) that had also been cleaved with HindIII and SmaI. A resulting plasmid, which contained the 3.8 kb HindIII-SmaI fragment of pTJS75 joined to the 8 kb pMON503 fragment, was saved and called pMON505. The CaMV35S-NOS expression cassette from pMON316 (see FIG. 3) was isolated on a 2.4 kb StuI-HindIII fragment and mixed with pMON505 DNA that had been cleaved with StuI and HindIII.

The resulting plasmid pMON530 (see FIG. 16) was digested with BglII, and the 1 kb XhoII fragment carrying the TGMV coat protein coding sequence was inserted. A plasmid was identified that contained the 1 kb fragment in the sense orientation. This plasmid, designated "pMON401," carried a CaMV35S/TGMV-CP/NOS construct (see FIG. 16). By substantially the same procedure described in Example 2, tobacco plants were transformed with pMON401. Self-fertilization of these plants, which were resistant to kanamycin, yielded seedling progeny that can be assayed for virus resistance, pursuant to the approach detailed above.

EXAMPLE 9

Expression Vector for Anti-Sense RNA Complementary to TMV RNA

An experiment was conducted to insert the TMV-CP gene into the intermediate plasmid (pMON316) so as to produce RNA having an anti-sense polarity relative to the mRNA for the coat protein.

Figure 17:
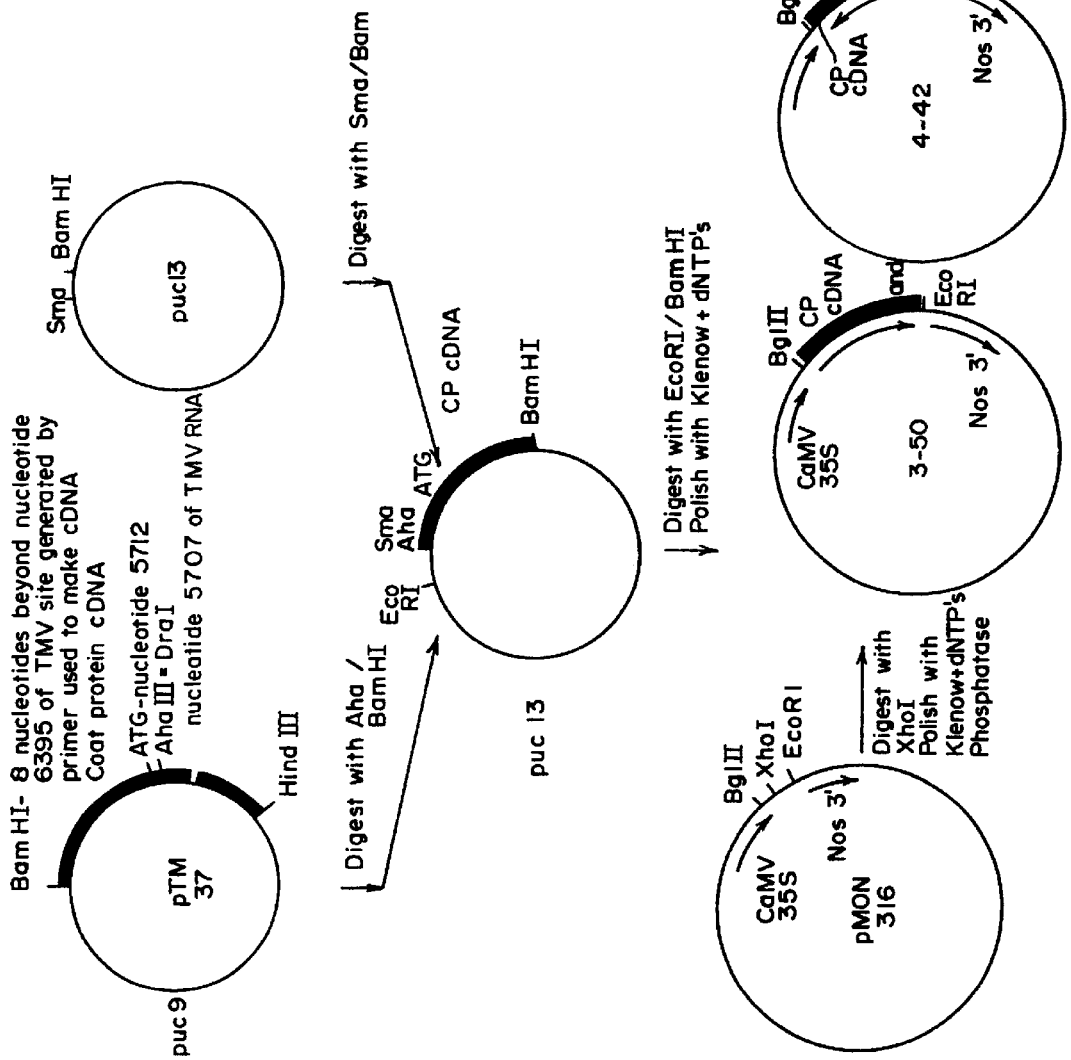
FIG. 17 is a diagrammatic representation of the steps employed in Example 9 to produce a plant vector containing DNA coding for an anti-sense complement to a TMV RNA.

With reference to FIG. 17, the TMV coat protein gene was excised from an intermediate plasmid (pTM37) with the enzyme AhaIII and BamHI. In this orientation, the 5' end of the gene encoding the mRNA is located near the AhaIII site. The AhaIII:BamHI fragment was introduced into plasmid pUC13 previously digested with BamHI and SmaI.

The coat protein gene was excised from pUC13 by digestion with EcoRI and BamHI. This fragment of DNA was ligated to pMON316 (see FIG. 3) restricted with the enzymes BglII and EcoRI.

In this configuration, the CaMV35S promoter would produce an RNA complementary to the TMV coat protein mRNA. The RNA would be comprised of (from the 5' end of the transcript):

(1) approximately 30 nucleotides derived from the CaMV35S promoter;

(2) approximately 8 nucleotides derived from the oligonucleotide primer used in preparing the first strand of cDNA;

(3) nucleotides (−) 6395 (−) 5707 of TMV RNA (Goelet et al (1982)); and (4) approximately 150 nucleotides contributed by the NOS 3' end.

This construct can be introduced into plants, and those plants assayed for virus resistance as described in Example 2.

EXAMPLE 10

Cloning of the Cucumber Mosaic Virus (CuMV) Coat Protein Gene

Size-fractionated genomic RNA of strain CUMV-D (available from J. M. Kaper, USDA Agricultural Research Service, Beltsville, Md.), enriched for RNA 4, was polyadenylated such that the estimated number of AMP residues per CUMV RNA molecule was about 30. In order to synthesize double-stranded CDNA, the methodology of Wickens et al (1978) was adapted to prepare first-strand CDNA. More specifically, 80/ul of a reaction mixture, containing 3/ug of the polyadenylated CuMV-RNA4, 100 mM Tris-HCl (pH 8.3), 140 mM Kcl, 10 mM $MgCl_2$, 19 mM beta-mercaptoethanol, 1.5/ug $(dT)_{15}$, 0.5 mM dNTP's, 20/uCi [alpha-$^{32}$P] dCTP (3000 Ci/mmole; New England Nuclear) and 48 units of AMV-reverse transcriptase (Life Sciences, Inc.), were incubated at 42° C. for 90 minutes. 4/ul of 0.5M EDTA were then added to the reaction mixture, which was subsequently extracted with phenol/chloroform and then back-extracted with 20/ul of 0.5 Tris-HCl (pH 7.5). The product was recovered free of nucleotides by two successive precipitations with one-third volume of 8M ammonium acetate and two volumes of ethanol.

The cDNA from the above reaction was dried and resuspended in 40/ul of water. Second-strand synthesis was adapted from Gubler & Hoffman (1983). The CDNA in 40/ul of water was added to the reaction mixture, which contained 20 mM Tris-HCl (pH 7.5), 10 mM $(NH_4)_2SO_4$, 5 mM $MgCl_2$, 100 mM KCl, 0.2 mg/ml BSA, 0.1 mM dNTP's, 30 units DNA polymerase I (New England Biolabs), 20/uCi [alpha-$^{32}$P] dCTP and 2 units of RNAse H (BRL) in a volume of 0.1 ml. This reaction mixture was first incubated at 11° C. for one hour, and then at 22° C. for one hour. The product was recovered in the same manner as described about for the synthesis of the first-strand cDNA.

Pursuant to the methods disclosed by Huynh et al (1985), the double-stranded cDNA was methylated with EcoRI methylase, ligated to phosphorylated EcoRI linkers (New England Biolab), digested with EcoRI enzyme, and then separated from excess linkers. The cDNA was thereafter electrophoresed on a 1% agarose gel, with marker DNA in flanking lanes. Markers were visualized by ethidium bromide staining, and a gel slice was excised containing cDNA of sizes approximately 900–1300 bp. The CDNA was electroeluted, precipitated in the presence of 5/ug of glycogen carrier (Boehringer Mannheim Biochemicals), and resuspended in a volume of $H_2O$ compatible with a 10/ul ligation reaction volume. The CDNA was then ligated at room temperature for four hours to 20 ng of EcoRI-digested, phosphatased pEMBL12(+) DNA. The resulting plasmids were then transformed into E. coli strain JM101. Colonies were selected by ampicillin resistance, as well as by white color on plates spread with 0.6 mg X-Gal and IPTG. Insert size was determined by EcoRI digestion of miniprep DNA (Maniatis et al (1982)).

Sixteen clones with inserts ranging between 600 and 1300 bp were further screened by dideoxy sequencing to determine the presence of sequences homologous to the CMV coat protein of strain X, as reported by Gould & Symons (1982). The longest clone was completely sequenced to confirm that full-length cDNA for CUMV CP had been obtained. The CuMV coat protein coding sequence can be cloned into the expression vectors pMON9818 and pMON9819 (see Example 7 above). These vectors can then be used to produce sense and antisense sequences from the CuMV coat protein coding sequence.

The following vectors were constructed and transferred into plants:

pMON9816—CuMV coat protein coding sequence in pMON9818 in sense orientation.

pMON9817—CUMV coat protein coding sequence in pMON9818 in antisense orientation.

These vectors were introduced into Agrobacterium cells, in accordance with Example 2, and transformed tomato and tobacco plants produced. These plants can be inoculated with CuMV, and the level of virus resistance determined, as described above.

EXAMPLE 11

Manipulation of RNA from Potato Leafroll Virus

Purified potato leafroll virus (PLRV) was obtained from Dr. Pete Thomas (USDA Agricultural Research Station, Prosser, Wash.), and intact viral RNA, about 6 kb in size, was isolated therefrom. This RNA can be polyadenylated using *E. coli* poly(A) polymerase; as described above, the first strand of the cDNA can then be synthesized by oligo dT priming. Thereafter, the second cDNA strand can be synthesized by use of DNA polymerase I in the presence of RNAse H, pursuant to Gubler & Hoffman (1983).

The double-stranded cDNA thus produced can be methylated with EcoRI methylase, ligated to EcoRI linkers, and then ligated to EcoRI-digested pEMBL12(+) in accordance with Example 10 above. The resulting plasmids can be transformed into *E. coli* JM101 (Messing & Vieira (1982)), and the recombinant clones thereby obtained can be screened by using antibodies against PLRV, as described by Thomas (1983). A cDNA segment identified as encoding the viral coat protein can be obtained by introducing a new restriction site and ATG translational initiator codon immediately adjacent (vis-a-vis the 5' end) to the codon for the $NH_2$-terminal amino acid of the mature coat protein. This can be accomplished via the method of Zoller & Smith (1982).

EXAMPLE 12

Manipulation of DNA From Cauliflower Mosaic Virus

The coat protein coding sequence for cauliflower mosaic virus (CaMV) can be isolated on a 1.6 kb fragment by cleavage of plasmid pOS1 (Howarth et al (1981)) with AccI, followed by treatment with the Klenow fragment of DNA polymerase and cleavage with BamHI; the plasmid itself can be obtained from Dr. Robert Shepherd (University of Kentucky, Lexington). After the 1.6 kb fragment is subjected to electro-phoretic separation on a gel, it can be purified using an NA-45 membrane (Schleicher & Scheull, Keene, N.H.) and mixed with pMON316 DNA which has been digested with EcoRI, treated with the Klenow fragment and digested with BglII.

Treatment with ligase yields a recombinant plasmid containing the CaMV coat protein coding sequence, which plasmid can be used to transform cells as described above. Those cells carrying the plasmid with the coding sequence in the sense orientation can be identified by digestion of the plasmid DNA with HindIII, i.e., such DNA will display HindIII fragments of 1.1 and 0.7 kb, as well as a larger fragment from the rest of the plasmid. Plasmid DNA containing a correctly-oriented CaMV coat protein coding sequence can then be cloned and introduced into plant cells, which in turn can be regenerated into whole plants. The virus resistance of these transformed plants can be determined thereafter in accordance with the basic approach detailed previously. For example, the resistance of transformed tobacco plants can be assayed by inoculation with CaMV strains W260, W262 and W283, which infect tobacco (Gracia & Shepherd (1985)).

EXAMPLE 13

DNA Construct With the TMV Coat Protein Coding Sequence Controlled by the MAS (2') Promoter A DNA fragment carrying the MAS promoter was excised from plasmid pNW 34C-2-1 (Garfinkel et al (1981)), which carries the octopine-type pTiA6 plasmid BamHI 2 fragment with EcoRI (21,631) and ClaI (20,138). (The numbers in parentheses are the coordinates of the cleavage sites taken from the published sequence of the octopine-type Ti plasmid T-DNA sequence of Barker et al (1983a).) The resultant 1503 bp fragment was purified and inserted into EcoRI- and ClaI-cleaved pMON505 (Horsch & Klee (1986)) to produce pMON706. The NOS3' end was excised from pMON530 with BglII and BamHI. The 298 bp NOS3' fragment was introduced into the BglII site of pMON706, adjacent to the 3' end of the MAS promoter, to produce pMON707.

The resulting MAS promoter-NOS3' cassette in pMON707 was transferred to a cointegrating-type vector by cleaving pMON707 with StuI and HindIII and then isolating the 3.2 kb fragment which carried the NOS-NPTII'-NOS chimeric kanamycin resistance gene and the MAS promoter-NOS3' cassette. This fragment was added to the 7.7 kb StuI-to-HindIII fragment of pMON200. The resulting plasmid, pMON9741, is analogous to pMON316 but contains an expression cassette wherein the MAS promoter replaces the CaMV35S promoter.

The TMV-CP coding sequence can be obtained as described in Example 2, or by digestion of pTM319 DNA with BglII and BamHI, as disclosed by Abel et al (1986). The 700 bp CP-encoding fragment can then be inserted into pMON9741 that has been cleaved with BglII. A plasmid with the CP insert in the sense orientation with respect to the promoter and NOS3' can be identified by digestion of the plasmid DNA with Blg II and EcoRI to release the MAS promoter on a 1.5 kb fragment and the CP coding sequence on a fragment of 700 bp. The resulting plasmid can then be mated into *A. tumefaciens*, and the *A. tumefaciens* cells carrying the MAS/TMV-CP/NOS3' construct used to obtain transformed tobacco and tomato plants as described above. The transformed plants can be assayed for virus resistance in the manner described previously.

EXAMPLE 14

Transformation of Plant Cells With Free DNA Vectors Using An Electorporation Technique The following description outlines a non-Agrobacterium-based, free DNA-delivery procedure to effect introduction, for purposes of obtaining virus disease resistance, of plasmid DNA into a variety of plant cells from which the outer membranes are removed (protoplasts).

A. Protoplast Isolation and Culture in Dicotyledon Species

Cultures of cells from soybean [*Glycine max* (GM)], petunia [*Petunia hybrida* Mitchell (MP4)] and carrot [*Daucus carota* (TC)] were grown, following Widholm (1977), in 250 ml Erlenmeyer flasks on gyratory shakers (135 rpm; 27°–28° C.), in 50 ml of MS culture medium (Murashige & Skoog (1962)) which contained 0.4 mg/l, 2,4-D for TC and GM, or 0.2 mg/l p-chlorophenoxy-acetic acid for MP4.

Protoplasts from GM and TC were produced, respectively, by incubating 10 ml packed cell volume of exponentially-growing, suspension culture cells for about 12 hours in 40 ml of enzyme dissolved in 10% mannitol and 0.1% $CaCl_2.2H_2O$ (pH 5.7). The enzyme mixture contained 2% Cellulase R-10 (Kinki Yakult, Nishinomiya, Japan), 0.1% Macerozyme R-10 (Kinki Yault) and 0.5% Pectolayase Y-23 (Seishin Pharmaceutical Co. Ltd., Noda, Chiba, Japan). The resulting protoplasts were isolated, purified and cultured as disclosed by Hauptmann & Widholm (1982).

Mesophyll protoplasts from MP4 were isolated and cultured as disclosed by Fraley et al (1984), except that the enzyme mixture used was the same as that employed for the suspension cultures.

B. Protoplast Isolation and Culture in Monocotyledon Species

Monocot cells were taken from wheat [*Triticum monococcum* (TM) and *Triticum aestiuum* (TA), as disclosed by Maddock et al (1983) and Ozias-Akins & Vasil (1983)], elephant grass [*Pennisetum purpureum* (PP), as disclosed by Vasil et al (1983) and Karlsson & Vasil (1986)], guinea grass [*Panicum maximum* (PM), as disclosed by Lu & Vasil (1981) and Karlsson & Vasil (1986)], rice [*Oryza sativa* (OS), as disclosed by Heyser et al (1983) and Yamada et al (1986)], corn [*Zea mays* (ZM), as disclosed by Meadows (1982)], sugarcane [*Saccharum officinarum* (SC), as disclosed by Ho & Vasil (1983) and Srinivasin & Vasil (1985)], and a double cross trispecific hybrid, disclosed by Dujardin & Hanna (1984), between *Pennisetum americanum, P. purpureum*, and *P. squamulatum* (PAPS). Suspension cultures of PM and PAPS were grown in a modified MS medium (Vasil & Vasil (1981)) containing 5% coconut milk and 2 mg/l 2,4-D, while the MS medium used for SC cultures contained an additional 500 mg/l casein hydrolysate. The TM suspension culture was grown in liquid medium in accordance with Dudits et al (1977). The other monocot cell cultures were grown as disclosed, respectively, in the above-cited references. Except for TM and PAPS, which were subcultured twice weekly, all suspension cultures were grown on a 7-day subculture regimen, with a 2–8 ml inoculum in 35 ml of medium. Prior to protoplast isolation, the suspensions were subcultured on the fourth to fifth day with a 5–8 ml inoculum in 25–35 ml medium.

Protoplasts for each monocot cell-type were isolated, as disclosed by Vasil et al (1983), using various enzyme mixtures dissolved in 3 mM MES, 0.45 M mannitol, 7 mM $CaCl_2.2H_2O$, and 0.7 mM $NaH_2PO_4OH$ (pH 5.6). The enzyme mixtures included 1.0% Cellulase RS (Kinki Yakult), and 0.8% pectinase (Sigma) for TM and PM; 2% Cellulase RS and 0.7% pectinase for SC; 3% Cellulase R-10 and 0.7% pectinase for PP; and 2.5% Cellulase R-10 and 0.75% Pectinase for PAPS.

The isolated monocot protoplasts were then cultured in 8p medium (Vasil & Vasil (1980)), as modified by Kao & Michayluk (1975). The culture medium contained 0.4–0.5 M glucose, 0.5–1.0 mg/l 2,4-D and 0.2 mg/l zeatin, and was diluted 1:2.3 with protoplast culture medium after 1 week. To determine plating efficiency of PAPS and TM, the equivalent of 2 ml of the original protoplast culture were diluted to 36 ml with suspension culture medium that contained 0.4% Seaplaque agarose (FMC) after 2–3 weeks. Three ml of the diluted culture were then plated over a layer of the same medium containing 0.6% agarose in a 10 cm petri dish.

C. Free DNA Delivery by Electroporation

In the presence of plasmid DNA containing the kanamycin resistance gene, protoplasts were electroporated using the Zimmerman Cell Fusion System (GCA Precision) or a capacitor discharge bank (Fromm et al (1985)). Electroporation with the Zimmerman Cell Fusion System was performed in a Zimmerman Helical Fusion Chamber or in an electroporation chamber constructed out of cuvettes and platinum or aluminum foil, following the method of Potter et al (1984). Pulses (240 V DC) were delivered, at 999.9/usec, in series of 9 pulses each. Each series of pulses was delivered 1, 10, 50 and 100 times, respectively, in the presence of 14/ug of plasmid DNA, with and without 50/ug of calf thymus DNA, in the protoplast wash solution.

A capacitor bank was constructed to contain four each of 40, 110, 240 340/UF capacitors, along with one 100 and one 2400/uF capacitor (Mallory); the capacitors could be charged and discharged individually or in parallel. The pulse discharge was monitored using a dual-channel recording oscilloscope (Tectronics model 584B). Amperage was determined by measuring the discharge across a 1 ohm resistor during electroporation.

Prior to electroporation, the protoplasts were washed once in 10 mM Hepes, 150 mM NaCl, 5 mM $CaCl_2$, and 0.2 M mannitol (pH 7.2), and then were brought to a density of approximately $3 \times 10^6$ protoplasts/ml using the same buffer (Fromm et al (1985)). To 1 ml of resuspended protoplats, 20/ug of plasmid DNA were added and mixed. The protoplasts were electroporated using various voltages and capacitances. The protoplasts were maintained on ice for approximately 10 minutes, after which the plating in liquid culture medium was effected.

To estimate the number of dicot protoplasts that were lysed by various electroporation treatments, the density of TC protoplasts was determined prior to, and immediately after, delivering of the pulse discharge; the measured values were expressed as percent survival. Viability determinations were based on phenosafranin dye exclusion, as disclosed by Widholm (1972), two days after electroporation. The results were expressed as percent viability compared to a non-electroporated control. An estimate of plating efficiency of electroporated monocot protoplasts was obtained by counting the number of colonies formed after 3–4 weeks of culture, and was expressed as percent of a non-electroporated control.

Transformed colonies were selected after transfer to medium containing kanamycin, as disclosed by Fromm et al (1986). In the same fashion, plasmids such as pMON319, pMON401, pMON9800, pMON9809 and pMON9816 which contain an engineered virus coat protein and the kanamycin-selectable marker can be used for free DNA transformation. Regenerated plants can be monitored for coat protein mRNA and protein production, using the procedures described in Example 2.

REFERENCES

Abel, P., et al, *Science* 232: 738 (1986).
Ammirato, P. V., et al (eds.), 3 HANDBOOK OF PLANT CELL CULTURE—CROP SPECIES (Macmillan Publ. Co. 1984).
Barker, R. F., et al, *Plant Molec. Biol.* 2:335 (1983a).
Barker, R. F., et al, *Nucleic Acids Research* 11: 2881–891 (1983b).
Beachy, R. N., et al, in BIOTECHNOLOGY IN PLANT SCIENCE—RELEVANCE TO AGRICULTURE IN THE EIGHTIES 265–75 (M. Zaitlin, et al eds.) (Academic Press 1985).
Bevan, M., et al, *Nature* 304: 184 (1983).
Bisaro, D. M., et al, *Nucleic Acid Res.* 10: 4913–922 (1982).
Bruening, G., et al, *Virology* 71: 498–517 (1976).
Costa, A. S., et al, *Plant Disease* 64: 538–41 (1980).
Covey, S., et al, *Nucleic Acid Res.* 9: 6735 (1981).
Duditis, D., et al, *Theoret. Appl. Genet.* 51: 127–32 (1977).
Dudley, R., et al, *Virology* 117: 19 (1982).
Dujardin, M. & W. Hanna, *Theoret. Appl. Genet.* 69: 97–100 (1984).
Fraley, R. T., et al, *Plant Mol. Biol.* 3: 371–78 (1984).
Fraley, R. T., et al, *Bio/Technology* 3: 629–35 (1985).
Franck, A., et al, *Cell* 21: 285 (1980).
Fromm, M., et al, *Proc. Natl. Acad. Sci. USA* 82: 824–28 (1985).
Fromm, M., et al, *Nature* 319: 791–93 (1986).
Gardner, R. C., et al, *Nucleic Acid Res.* 9: 2871 (1981).
Garfinkel, D., et al, *Cell* 27: 143–53. (1981).
Goelet, P., et al, *Proc. Natl. Acad. Sci. USA* 79: 5818 (1982).
Gould, A. R. & R. H. Symons, *Eur. J. Biochem.* 126: 217–26 (1982).
Gracia, O. & R. Shepherd, *Virology* 146: 141–45 (1985).
Gubler, U. & B. J. Hoffman, *Gene* 25: 263–69 (1983).
Guilley, H., et al, *Cell* 30: 763 (1982).
Hamer, D. & P. Leder, *Cell* 18: 1299–1302 (1979).
Hamilton, W. D. O., et al, *EMBO J.* 3: 2197–205 (1984).
Hauptman, R. M. & J. M. Widholm, *Plant Physiol.* 70: 30–34 (1982).
Herrera-Estrella, L., et al, *Nature* 303: 209 (1983).
Heyser, J., et al, *Plant Sci. Letters* 29: 175–82 (1983).
Hirth, L. & K. E. Richards, in Lauffer, et al (1981).
Ho, W. & I. K. Vasil, *Am. Bot.* 51: 719–26 (1983).
Horsch, R. B., et al, *Science* 227: 1229 (1985).
Horsch, R. B. & H. Klee, *Proc. Natl. Acad. Sci. U.S.A.* 83: 4428–32 (1986).
Howarth, A., et al, *Virology* 112: 678 (1981).
Huynh et al, in 1 DNA CLONING (D. Glover ed.) IRL Press 1985).
Kao, K. N., and Michayluk, M. R., (1975) *Planta* 126, 105–110.
Kado, C. I. & H. O. Agrawal, PRINCIPLES AND TECHNIQUES IN PLANT VIROLOGY (Van Nostrand Rheinhold 1972).
Karlsson, S. B. & I. K. Vasil, *J. Plant Physiol.* 123: 211–27 (1986).
Klee, H. J., et al, *Bio/Technology* 3: 637–42 (1985).
Laemmli, U. K., *Nature* 227:680–85 (1970).
Lane, B. G. & T. D. Tremaites-Kennedy, *Eur. J. Biochem.* 114: 457–63 (1981).
Lauffer, M. A., et al (eds.), 26 ADVANCES IN VIRUS RESEARCH (Academic Press 1981).
Lu, C. & I. K. Vasil, *Ann. Bot.* 48: 543–48 (1981).
Maddock, S., et al, *J. Exp. Bot.* 34: 915–26 (1983).
Maniatis, T., et al (eds.), MOLECULAR CLONING: A LABORATORY MANUAL (Cold Spring Harbor Labs 1982).
Matthews, R. E. F., PLANT VIROLOGY (Academic Press 1981).
Meadows, M., *Plant Sci. Letters* 28: 337–48 (1982).
Messing, J. & J. Vieira, *Gene* 19: 269 (1982).
Moore, S., in 14 THE ENZYMES—NUCLEIC ACIDS (Part A) 281–85 (Academic Press 1981).
Murashige T. & F. Skoog, *Physiol. Plant.* 15: 473–497 (1962).
Odell, J., et al, *Nature* 313: 810 (1985).
Ozias-Akins, P. & I. K. Vasil, *Amer. J. Bot.* 70: 1092–97 (1983).
Potter, H., et al, *Proc. Natl. Acad. Sci. U.S.A.* 81: 7161–165 (1984).
Rast, A., et al, Netherlands *J. Plant Pathology* 78: 110–12 (1972).
Rogers, S. G., *Plant Molecular Biology Report* 3: 111–16 (1985).
Rogers, S., et al, in 118 METHODS IN ENZYMOLOGY 627 (H. Weissbach & A. Weissbach, eds.) (Academic Press 1986).
Rogers, S. G., et al, in BIOTECHNOLOGY IN PLANT SCIENCE 210 (P. Day, et al eds.) (Academic Press 1985).
Sandmerer, E. & P. Christen, *J. Biol. Chem.* 255: 6153–59 (1980).
Schmidhauser, T. J. & D. R. Helinski, *J. Bacteriol.*: 164–155 (1985).
Shaw, G. & R. Kamen, *Cell* 46: 659–67 (1986).
Srinivasan, C. & I. K. Vasil, *Am. J. Bot.* 72: 833 (1985).
Symington, J., et al, *Proc. Natl. Acad. Sci. USA* 78: 177–181 (1981).
Thomas, P. E., *Plant Disease* 67: 744–47 (1983).
Towbin, et al, *Proc. Natl. Acad. Sci. U.S.A.* 76: 4350 (1979).
Tumer, N., et al, *Nucl. Acids Res.* 14: 3325 (1986).
Vance, V. B. & R. N. Beachy, *Virology* 132: 271–81 (1984).
Vasil, V. & I. K. Vasil, Theoret. Appl. Genet 56: 97–99 (1980).
Vasil, V. & I. K. Vasil, *Ann Bot.* 47: 669–78 (1981).
Vasil, V., et al, *Z. Pflanzenphysiol.* 111: 233–239 (1983).
Wickens, M. P., et al, *J. Biol. Chem.* 253: 2483–495 (1978).
Widholm, J. M., *Stain Technol.* 47: 189–94 (1972).
Widholm, J. M., *Planta* 134: 103–8 (1977).
Yamada, Y., et al, *Plant Cell Reports* 5: 85–88 (1986).
Zakharyiev, V. M., et al, *Curr. Trends Life Sci.* 12: 61–70 (1984).

Zoller, M. & M. Smith, *Nucleic Acids Res.* 10: 6487 (1982).
Zurini, M., et al, *J. Biol. Chem.* 259: 618–27 (1984).

What is claimed is:

1. A method of producing genetically transformed plant cells which are resistant to infection by a plant virus, comprising the steps of:
   (a) inserting into the genome of a plant cell a recombinant, double-stranded DNA molecule comprising
      (i) a promoter which functions in plant cells to cause the production of RNA sequences of said plant virus;
      (ii) a DNA sequence that causes the production of an RNA sequence, said RNA sequence encoding the coat protein of said plant virus; and
      (iii) a 3' non-translated region which functions in plant cells to cause the addition of polyadenylated nucleotides to the 3' end of said RNA sequence; and
   recovering transformed plant cells which have increased resistance to infection by said plant virus.

2. A method of claim 1, wherein said promoter is a plant DNA virus promoter.

3. A method of claim 2, wherein said promoter is a 35S promoter of cauliflower mosaic virus.

4. A method of claim 1, wherein said promoter is a nopaline synthase or octopine synthase promoter.

5. A method of claim 1, wherein said promoter is a plant gene promoter.

6. A method of claim 5, wherein said promoter is a ribulose bis-phosphate carboxylase small subunit promoter.

7. A method of claim 1, wherein said promoter was a promoter of a gene encoding a hydroxyproline-rich glycoprotein.

8. A method of claim 1, wherein said plant virus is selected from the group consisting of tobacco mosaic, soybean mosaic, bean pod mottle, barley yellow dwarf, wheat streak, wheat spindle streak, soil born mosaic, maize dwarf mosaic, maize chlorotic dwarf, potato virus X, potato virus Y, potato leafroll, and tomato golden mosaic virus.

9. A method of claim 8, wherein said plant virus is tobacco mosaic virus.

10. A method of claim 1, wherein said DNA sequence is expressed in said transformed plant cells, such that said coat protein is present in said transformed plant cells.

11. A recombinant, double-stranded DNA molecule comprising in sequence:
   (a) a promoter which functions in plant cells to cause the production of RNA sequences of a plant virus;
   (b) a DNA sequence that causes the production of an RNA sequence, said RNA sequence encoding the coat protein of said plant virus; and
   (c) a 3' non-translated region which functions in plant cells to cause the addition of polyadenylated nucleotides to the 3' end of said RNA sequence,
said molecule being incapable of causing systemic infection in plants.

12. A DNA molecule of claim 11, wherein said promoter is heterologous with respect to the coat protein coding sequence.

13. A DNA molecule of claim 11, wherein said promoter is a plant DNA virus promoter.

14. A DNA molecule of claim 13, wherein said promoter is the 35S promoter of cauliflower mosaic virus.

15. A DNA molecule of claim 11, wherein said promoter is a nopaline synthase or octopine synthase.

16. A DNA molecule of claim 11, wherein said promoter is a plant gene promoter.

17. A DNA molecule of claim 16, wherein said promoter is a ribulose bis-phosphate carboxylase small subunit promoter.

18. A DNA molecule of claim 11, wherein said promoter was a promoter of a gene encoding a hydroxyproline-rich glycoprotein.

19. A DNA molecule of claim 11, wherein said plant virus is selected from the group consisting of tobacco mosaic, soybean mosaic, bean pod mottle, barley yellow dwarf, wheat streak, wheat spindle streak, soil born mosaic, maize dwarf mosaic, maize chlorotic dwarf, potato virus X, potato virus Y, potato leafroll, and tomato golden mosaic virus.

20. A plant transformation vector comprising a DNA molecule of claim 11.

21. A bacterial cell comprising a plant transformation vector of claim 20.

22. A bacterial cell of claim 21, wherein said transformation vector is the pMON319::pTiB6S3-SE cointegrate plasmid.

23. A bacterial cell of claim 21, wherein said bacterial cell is an *Agrobacterium tumefaciens* cell.

24. A bacterial cell of claim 23, assigned ATCC deposit accession No. 53924.

25. A transformed plant cell consisting chromosomal DNA comprised of:
   (a) a promoter which functions in, plant cells to cause the production of RNA sequences of a plant virus;
   (b) a DNA sequence that causes the production of an RNA sequence, said RNA sequence encoding the coat protein of said plant virus; and
   (c) a 3' non-translated region which functions in plant cells to cause the addition of polyadenylated nucleotides to the 3' end of said RNA sequence.

26. A plant cell of claim 25, said plant cell exhibiting resistance to said plant virus.

27. A plant cell of claim 26, wherein said DNA sequence is expressed by said plant cell such that, said coat protein is present in said plant cell.

28. A plant cell of claim 26, said plant cell being from a family selected from the group consisting of Leguminosae, Umbelliferae, Cruciferae, Cucurbitaceae, Gramineae, and Solanaceae.

29. A plant cell of claim 26, wherein said plant virus is tobacco mosaic virus.

30. A plant cell of claim 29, said plant cell being a tobacco cell.

31. A plant cell of claim 29, said plant cell being a tomato cell.

32. A method of claim 1, wherein said promoter is a mannopine synthase promoter.

33. A DNA molecule of claim 11, wherein said promoter is a mannopine synthase promoter.

34. A method of claim 1, wherein step (a) comprises Agrobacterium-mediated insertion of said DNA molecule into a plant cell that is susceptible to infection by *Agrobacterium tumefaciens*.

35. A transformed plant cell of claim 25, wherein said cell is susceptible to infection by *Agrobacterium tumefaciens*.

36. A method of claim 1, wherein said plant cell is from a plant selected from the group consisting of potato, tomato, pepper, tobacco, soybean, wheat, corn, citrus, squash, cucumber and beet.

37. A cell of claim 26 which is from a plant selected from the group consisting of potato, tomato, pepper, tobacco, soybean, wheat, corn, citrus, squash, cucumber and beet.

38. A recombinant, double-stranded DNA molecule comprising in sequence:
   (a) a promoter which functions in plant cells to cause the production of RNA sequences of a plant virus;

(b) a DNA sequence that causes the production in an RNA sequence, said RNA sequence encoding the coat protein of said plant virus; and (c) a 3' non-translated region which functions in plant cells to cause the addition of polyadenylated nucleotides to the 3' end of said RNA sequence, said promoter being from a source other than cauliflower mosaic virus.

39. A virus-resistant dicotyledonous plant comprising in its chromosomal genome a DNA construct comprising a viral coat protein structural gene downstream from a plant-expressible promoter.

40. A method for producing a virus-resistant dicotyledonous plant, comprising the steps of:

(a) introducing into the chromosomal genome of a dicotyledonous plant cell a recombinant DNA molecule comprising a viral coat protein structural gene downstream from a plant-expressible promoter;

(b) recovering transformed plant cells; and (c) regenerating virus-resistant dicotyledonous plants from said transformed cells.

* * * * *

UNITED STATES PATENT AND TRADEMARK OFFICE
CERTIFICATE OF CORRECTION

PATENT NO.    : 6,608,241 B1
DATED         : August 19, 2003
INVENTOR(S)   : Roger N. Beachy, Robert T. Fraley and Stephen G. Rogers It is certified that error appears in the above-identified patent and that said Letters Patent is hereby corrected as shown below:

<u>Column 27,</u>
Line 17, before the word "recovering" insert -- (b) --.
Line 28, delete "was" and insert -- is -- therefor.

<u>Column 28,</u>
Line 21, delete "consisting" and insert -- comprising -- therefor.
Line 23, delete the comma "," after "in".
Line 35, delete the comma "," after "that".

Signed and Sealed this

Second Day of December, 2003

JAMES E. ROGAN
*Director of the United States Patent and Trademark Office*